US009175136B2

(12) United States Patent
Louis

(10) Patent No.: US 9,175,136 B2
(45) Date of Patent: *Nov. 3, 2015

(54) METHOD FOR THE MANUFACTURE OF POLY(ARYL ETHER KETONE)S IN THE PRESENCE OF SODIUM CARBONATE

(75) Inventor: Chantal Louis, Alpharetta, GA (US)

(73) Assignee: Solvay Advanced Polymers, L.L.C., Alpharetta, GA (US)

( * ) Notice: Subject to any disclaimer, the term of this patent is extended or adjusted under 35 U.S.C. 154(b) by 243 days.

This patent is subject to a terminal disclaimer.

(21) Appl. No.: 13/125,537

(22) PCT Filed: Oct. 23, 2009

(86) PCT No.: PCT/EP2009/064011
§ 371 (c)(1),
(2), (4) Date: Apr. 21, 2011

(87) PCT Pub. No.: WO2010/046484
PCT Pub. Date: Apr. 29, 2010

(65) Prior Publication Data
US 2011/0213095 A1 Sep. 1, 2011

Related U.S. Application Data

(60) Provisional application No. 61/108,096, filed on Oct. 24, 2008, provisional application No. 61/108,097, filed on Oct. 24, 2008, provisional application No. 61/140,205, filed on Dec. 23, 2008.

(51) Int. Cl.
*C08G 65/40* (2006.01)
*C07C 315/06* (2006.01)
*C08G 8/02* (2006.01)
*C08G 75/23* (2006.01)

(52) U.S. Cl.
CPC .......... *C08G 65/4093* (2013.01); *C07C 315/06* (2013.01); *C08G 8/02* (2013.01); *C08G 65/4012* (2013.01); *C08G 65/4087* (2013.01); *C08G 75/23* (2013.01); *C08G 2261/3444* (2013.01)

(58) Field of Classification Search
CPC .......... C08G 2650/40; C08G 65/4087; C08G 65/4012
USPC ........................................... 528/219, 86, 222
See application file for complete search history.

(56) References Cited

U.S. PATENT DOCUMENTS

| 3,655,331 | A | * | 4/1972 | Seglin et al. ................... 423/207 |
| 3,904,733 | A | * | 9/1975 | Gancy et al. ................. 423/206.2 |
| 4,113,698 | A | * | 9/1978 | Staniland ......................... 528/481 |
| 4,151,261 | A | * | 4/1979 | Poncha et al. ............. 423/206.2 |
| 4,176,222 | A | * | 11/1979 | Cinderey et al. ............... 528/126 |
| 4,320,224 | A | | 3/1982 | Rose et al. |
| 4,331,798 | A | | 5/1982 | Staniland |
| 4,636,557 | A | | 1/1987 | Deckers |
| 4,638,044 | A | * | 1/1987 | Kelsey ............................ 528/125 |
| 4,731,429 | A | * | 3/1988 | McMaster et al. ............. 528/127 |
| 4,766,197 | A | * | 8/1988 | Clendinning et al. ........ 528/125 |
| 4,767,837 | A | * | 8/1988 | Jansons .......................... 528/125 |
| 4,774,311 | A | * | 9/1988 | Kelsey ............................ 528/125 |
| 4,855,388 | A | * | 8/1989 | Kelsey ............................ 528/125 |
| 4,867,912 | A | * | 9/1989 | Heinz et al. ................... 528/125 |
| 4,868,273 | A | | 9/1989 | Daniels |
| 4,906,784 | A | * | 3/1990 | Skoler ............................ 528/125 |
| 4,908,425 | A | * | 3/1990 | Robeson et al. .............. 528/125 |
| 4,952,665 | A | * | 8/1990 | Ebata et al. .................... 528/219 |
| 4,999,414 | A | * | 3/1991 | Genz et al. .................... 528/125 |
| 5,081,214 | A | | 1/1992 | Schneller |
| 5,116,933 | A | * | 5/1992 | Newton ......................... 528/125 |
| 5,120,818 | A | * | 6/1992 | Robeson et al. .............. 528/125 |
| 5,122,587 | A | * | 6/1992 | Heinz et al. ................... 528/126 |
| 5,122,588 | A | * | 6/1992 | Koch et al. .................... 528/179 |
| RE34,085 | E | * | 9/1992 | Rose et al. .................... 528/125 |
| 5,194,561 | A | | 3/1993 | Fischer et al. |
| 5,212,278 | A | * | 5/1993 | Pfaendner et al. ............ 528/171 |
| 5,268,444 | A | * | 12/1993 | Jensen et al. .................. 528/125 |
| 5,362,836 | A | * | 11/1994 | Helmer-Metzmann et al. .......... 528/125 |
| 5,373,081 | A | * | 12/1994 | Yang et al. .................... 528/125 |
| 5,523,384 | A | * | 6/1996 | Memeger et al. ............. 528/392 |
| 5,580,948 | A | * | 12/1996 | Neufeld et al. ............... 528/125 |
| 6,593,445 | B2 | * | 7/2003 | Schwab ......................... 528/175 |
| 2002/0010307 | A1 | * | 1/2002 | Schwab ......................... 528/174 |
| 2009/0240020 | A1 | * | 9/2009 | Gharda et al. ................. 528/126 |
| 2011/0201775 | A1 | * | 8/2011 | Louis et al. ................... 528/126 |

(Continued)

FOREIGN PATENT DOCUMENTS

| CN | 101215365 A | 7/2008 |
| DE | 4121139 A1 | 1/1993 |
| EP | 0001879 A1 | 5/1979 |

(Continued)

OTHER PUBLICATIONS

U.S. Appl. No. 13/125,508, filed Apr. 21, 2011, Chantal Louis et al.
U.S. Appl. No. 13/125,523, filed Apr. 21, 2011, Chantal Louis.
Zhuo, Ni, et al—"Characterization and Spectra Studies of Peek Prepared by Two Salting Ways", Polymer Materials Science and Engineering, 1989, n° 3, p. 64-68; 5 pgs; Includes abstract in English.
Nassau Kurt—"Color", Kirk-Othmer Encyclopedia of Chemical Technology, 2004, vol. 7, p. 303-341, John Wiley & Sons, Inc.; 39 pgs.
"Solvay Process", Wikipedia, the Free Encyclopedia, "http://en.wikipedia.org/wiki/Solvay_process", Nov. 21, 2008; 8 pgs.

(Continued)

*Primary Examiner* — Liam J Heincer
(74) *Attorney, Agent, or Firm* — Osha • Liang LLP

(57) ABSTRACT

Sodium carbonate ($Na_2CO_3$) having a certain particle size distribution and its use in preparing poly(aryl ether ketone)s, especially PEEK. Poly(aryl ether ketone)s made using the described sodium carbonate. A method for providing a sodium carbonate having a certain particle size distribution, which is especially well suited for the preparation of poly (aryl ether ketone)s.

13 Claims, No Drawings

(56) References Cited

U.S. PATENT DOCUMENTS

| | | | |
|---|---|---|---|
| 2011/0213115 A1* | 9/2011 | Louis | 528/126 |
| 2011/0224399 A1* | 9/2011 | Louis et al. | 528/126 |

FOREIGN PATENT DOCUMENTS

| | | |
|---|---|---|
| EP | 0194062 A2 | 9/1986 |
| EP | 211693 A1 | 2/1987 |
| EP | 0303389 A2 | 2/1989 |
| EP | 2292673 A1 | 3/2011 |
| GB | 2217322 A | 10/1989 |
| WO | 95/31502 A1 | 11/1995 |
| WO | WO 0166620 A2 | 9/2001 |
| WO | WO 2009021918 A1 | 2/2009 |
| WO | WO 2010046482 A1 | 4/2010 |
| WO | WO 2010046483 A1 | 4/2010 |
| WO | WO 2010046487 A1 | 4/2010 |

OTHER PUBLICATIONS

International Search Report and Written Opinion issued Feb. 15, 2010 in corresponding International Application No. PCT/EP2009/064011 (10 pages).

International Preliminary Report on Patentability issued Apr. 26, 2011 in corresponding International Application No. PCT/EP2009/064011 (7 pages).

Communication pursuant to Article 94(3) EPC issued Feb. 2, 2012 in corresponding European application No. 09 737 003.5 (5 pages).

Communication pursuant to Article 94(3) EPC issued Jan. 10, 2013 in corresponding European application No. 09 737 003.5 (3 pages).

Sodium carbonate—a versatile material; published by the Royal Society of Chemistry; "Manufacturing sodium carbonate—an overview for teachers" (2 pages).

Sodium Carbonate; SIDS Initial Assessment Report for SIAM 15; Boston, USAA, Oct. 22-25, 2002; UNEP Publications (22 pages).

Technical Data Sheet—Light Sodium Carbonate; NovaCarb; Jan. 2004 (2 pages).

* cited by examiner

METHOD FOR THE MANUFACTURE OF POLY(ARYL ETHER KETONE)S IN THE PRESENCE OF SODIUM CARBONATE

CROSS-REFERENCE TO RELATED APPLICATIONS

The present application is a U.S. national stage entry under 35 U.S.C. §371 of International Application No. PCT/EP2009/064011 filed Oct. 23, 2009, which claims the priority benefit to U.S. provisional application No. 61/108,096 filed on Oct. 24, 2008, to U.S. provisional application No. 61/108,097 filed on Oct. 24, 2008, and to U.S. provisional application No. 61/140,205 filed on Dec. 23, 2008, the whole content of all these applications being herein incorporated by reference for all purposes.

FIELD OF THE INVENTION

The present invention relates to the use of a sodium carbonate ($Na_2CO_3$) having a certain particle size distribution in preparing poly(aryl ether ketone)s, especially PEEK. Poly(aryl ether ketone)s made using said sodium carbonate also make up a part of the invention, as well as compositions of matters and shaped articles comprising said poly(aryl ether ketone)s.

The present invention relates also to a method for providing a sodium carbonate having a certain particle size distribution, which is especially well suited for the preparation of poly(aryl ether ketone)s.

BACKGROUND OF THE INVENTION

Poly(aryl ether ketone)s (i.e., PAEKs) are a well known class of engineering polymers useful in various fields of endeavor. Poly(ether ether ketone) (PEEK) and poly(ether ketone) (PEK) are the most common PAEKs. PEK and PEEK are high-strength, radiation-resistant engineering plastics whose structures combine both ether and ketone groups. Both are thermally stable and highly resistant to chemicals. Generally, PAEKs are prepared by aromatic nucleophilic substitution. For example, p-hydroquinone can be used as a nucleophilic component which is deprotonated with a base such as NaOH, $Na_2CO_3$, $K_2CO_3$, or a combination of $Na_2CO_3$ and $K_2CO_3$. The resultant phenolate may then react with, e.g., an aromatic dihalocompound, in particular a dihalobenzophenone such as 4,4'-difluorobenzophenone to form a PAEK, e.g. PEEK, via nucleophilic substitution, with the halogen atoms of the dihalobenzophenone acting as leaving groups. Certain dinucleophiles other than p-hydroquinone commonly used as monomers in the synthesis of PAEKs are bisphenols such as 4,4'-dihydroxybenzophenone, 4,4'-biphenol, 1,4-bis(p-hydroxybenzoyl)benzene, 1,3-bis(p-hydroxybenzoyl)benzene, . . . . Aromatic trinucleophiles, aromatic poly(>3)-nucleophiles, aromatic trihalocompounds, aromatic poly(>3) halocompounds, and mixtures thereof can also be used, generally in addition to the aromatic dinucleophile and the aromatic dihalocompound, when a branched or cross-linked PAEK is to be synthesized.

Often, such PAEK reactions are carried out in a solvent; the solvent may be, or may contain, diphenylsulfone. Additionally, the reaction is often, but not always, carried out using a cosolvent which forms an azeotrope with water, to help the removal of water from the reaction mixture, such as p-xylene.

To the best of the inventor's knowledge, the effect of sodium carbonate particle size on the characteristics of a PAEK produced therewith has not been thoroughly or systematically investigated.

For example, U.S. Pat. No. 4,320,224 (Rose et al.) describes the preparation of PEEK by reacting 4,4'-difluorobenzophenone with p-hydroquinone in the presence of at least one alkali metal carbonate or bicarbonate. In particular, Rose's Example 3 (which was submitted for comparison purposes) describes a polymerization process for making PEEK using a certain anhydrous sodium carbonate as sole alkali metal carbonate or bicarbonate; the PEEK made accordingly suffered from a low IV (equal to 0.48) and a rather dark color (absorbance of 0.20). Precisely, Rose teaches, notably on col. 7, l. 46-50, that the formation of low molecular weight, dark-colored, brittle PEEK, results from the use of sodium carbonate or bicarbonate alone, and proposes, as sole remedies, to use instead a higher alkali metal carbonate or bicarbonate (such as $K_2CO_3$) either alone, or in admixture with $Na_2CO_3$. Unfortunately, Rose's proposed remedies are generally not as suitable as desired; indeed, the use of $K_2CO_3$ or another higher alkali metal has also some negative influence on polymer properties (resulting in gels and discolored polymer), as described in ICI Patent application EP001879, and in Zhuo N., Yubin Z., Zhongwen W., Xinyi T., Polymer Materials Science and Engineering, 1989, N 3, P 64-68. These ones are completely overlooked by Rose. Besides, Rose provides no information on the particle size distribution of the sodium carbonate of Example 3, except that that has been sieved through a 500 µm sieve; as a matter of fact, based on the low IV and dark color of the resulting PEEK, it can be concluded a posteriori, accounting for the Applicant's present contribution, that the sodium carbonate used by Rose had very likely a $D_{90}$ well above 250 µm. More precisely, considering that that the most broadly available sodium carbonates are by far dense sodium carbonates (of which the $D_{50}$ are typically of about 400 µm), it is very likely that Rose's sodium carbonate is a dense sodium carbonate that was sieved through a 500 µm sieve, and the sieving operation that was operated, did obviously not eliminate the big amount of particles having a diameter of 400 µm up to less than 500 µm which were contained in the dense sodium carbonate. Finally, it is noted that Rose does not provide any information on the possible importance that the particle size distribution of the alkali metal carbonate or bicarbonate may have on the PEEK polymerization process and polymer properties.

U.S. Pat. No. 4,636,557 is similar, using a combination of, e.g., sodium carbonate and calcium carbonate in the preparation of a PAEK and indicating that "the particle size of the carbonates used according to the invention is not in itself critical, but they are preferably used in a finely ground state and mostly have particle sizes smaller than 0.3 mm. The particle sizes are preferably between 1 and 250 µm". Although it is not clear exactly what carbonate particle sizes were used in the several Examples of U.S. Pat. No. 4,636,557, Example 1 (using potassium carbonate) indicates that the particles were "ground to a particle size of less than 0.3 mm".

U.S. Pat. No. 5,081,214 describes a process for the preparation of an aromatic polyether employing a mixture of sodium carbonate and sodium hydrogen carbonate. The reference states that the advantages achieved according to the invention are not dependent on the particle size of the carbonate compounds used, and further indicates that using a mixture of "coarse particle" soda having a particle size from 200 µm to 800 µm and sodium bicarbonate can help prevent unwanted dust formation during filling of the reaction vessel. The Examples of U.S. Pat. No. 5,081,214 use such "coarse particle" sodium carbonate while Comparative Examples use sodium carbonate having a particle size of 80 µm.

Finally, both U.S. Pat. Nos. 4,868,273 and 5,194,561 relate to the preparation of polyethers that can or must contain —$SO_2$— linking groups in the presence of sodium carbonate. In U.S. Pat. No. 4,868,273 the sodium carbonate is desirably used in a finely divided form in order to avoid a product with a lower inherent viscosity (IV). For example, using sodium carbonate particles all below 0.261 mm a polymer product with an IV of over 0.7 was obtained, whereas with at least 50% by weight of the particles over 0.376 mm the IV of the product obtained was less than 0.7.

U.S. Pat. No. 5,194,561 describes a process for the preparation of an aromatic polyether in which metal carbonates including sodium carbonate are used in the form of finely ground salts. U.S. '561 teaches that polyether sulfone synthesis can proceed satisfactorily using sodium carbonate having a $D_{90}$ value of about 50 μm; on the other hand, according to U.S. '561, polyether ketone synthesis would require a more finely ground material, with the preference being given to $D_{90}$ values of below 30 μm, in particular below 20 μm. The expressed requirements in terms of particle size would result from differences of reactivity of the monomers involved in the polycondensation reactions.

PAEKs are known for their exceptional balance of technical properties, namely high melting point, good thermal stability, high stiffness and strength, good toughness and really excellent chemical resistance. Therefore, PAEKs have potential for a wide variety of uses, and their favorable properties class them with the best of the engineering polymers. However, PAEKs currently available to the trade suffer from certain disadvantages.

PAEKs currently available to the trade have an inherent yellow to dark grey color as formed, which limits their use in certain specific applications where lighter colors are needed. PAEKs having an improved, lighter color could find wider acceptance for many applications where color is a concern. Lower color PAEKs are thus clearly needed by the art and would represent a significant improvement over the PAEKs currently available to the trade.

Moreover, PAEKs are very good candidates for medical applications. For these ones, the presence in the PAEKs of residues of toxic compounds like p-xylene, which, as above explained, is otherwise helpful for removing the water from the reaction mixture, should desirably be avoided or at least reduced to a minimum.

In addition, there is also a need for PAEK featuring an improved processability.

These and other needs are met by certain embodiments of the present invention.

SUMMARY OF THE INVENTION

The inventor has thoroughly and systematically investigated the effect of sodium carbonate particle size on the characteristics of a PAEK produced therewith, and have identified a particle size range that provides a PAEK with good properties, including superior color and, if desired, the lack of a cosolvent forming an azeotrope with water such as p-xylene when synthesizing the polymer. The present invention thus relates to sodium carbonate having a certain particle size range and its use in PAEKs manufacture, especially PEEK. PAEKs made using the sodium carbonate according to the present invention also make up a part of the invention, as well as compositions of matters and shaped articles comprising said PAEKs. Among other advantages, using sodium carbonate powder meeting these requirements allows one to synthesize easily high molecular weight PAEKs in the presence of a reduced amount, or even in the absence, of any other condensation auxiliary, while the presence of a substantial amount of such another additional condensation auxiliary, e.g. potassium carbonate may be necessary to synthesize high molecular weight PAEKs when sodium carbonate not meeting the requirements is used. As already mentioned, it is known that the use of $K_2CO_3$ has some negative influence on polymer properties (gels and discolored polymer).

The inventor has also unveiled an original and particularly advantageous method for providing a sodium carbonate having a certain particle size distribution, which is suitable for providing a PAEK with a good properties, including superior color and, if desired, the lack of a cosolvent forming an azeotrope with water such as p-xylene when synthesizing the polymer. This method for providing a performing sodium carbonate represents another important aspect of the present invention. As will be seen later on, the so-provided sodium carbonate is a light sodium carbonate. Hence, in relation herewith, the inventor has also proposed a new method for making the commerce of a light sodium carbonate suitable for providing a PAEK with a good properties, including superior color and, if desired, the lack of a cosolvent forming an azeotrope with water such as p-xylene when synthesizing the polymer, said method emphasizing the particular particle size distribution of the light sodium carbonate of concern.

Additional aspects and other features of the present invention will be set forth in part in the description that follows and in part will become apparent to those having ordinary skill in the art upon examination of the following or may be learned from the practice of the present invention. The advantages of the present invention may be realized and obtained as particularly pointed out in the appended claims. As will be realized, the present invention is capable of other and different embodiments, and its several details are capable of modifications in various obvious respects, all without departing from the present invention. The description is to be regarded as illustrative in nature, and not as restrictive.

DETAILED DESCRIPTION OF THE PREFERRED EMBODIMENTS

In a method according to the present invention, a poly(aryl ether ketone) is prepared by aromatic nucleophilic substitution in the presence of particulate sodium carbonate, wherein said particulate sodium carbonate has a particle size distribution as follows: $D_{90} \geq 45$ μm and $D_{90} \leq 250$ μm and $D_{99.5} \leq 710$ μm.

Nucleophilic substitution forms a well-known, fundamental class of substitution reaction in which a nucleophile (i.e. a chemical compound or group that is attracted to nuclei and tends to donate or share electrons) chemically reacts with an electrophile (i.e. a chemical compound or group that is attracted to electrons and tends to accept electrons), by selectively bonding with the positive or partially positive charge of an atom of the electrophile (for example, a carbon atom) and displacing a group or atom attached to the atom bearing the positive or partially positive charge (said displaced group or atom being commonly referred to as the leaving group). Dinucleophiles are compounds which comprise two nucleophilic groups, while dielectrophiles are compounds comprising two electrophilic groups.

This invented method comprises generally the condensation reaction between an aromatic dinucleophile and an aromatic dielectrophile, or the auto-condensation reaction of an aromatic compound comprising one electrophilic group and one nucleophilic group; an aromatic dinucleophile, an aromatic dielectrophile and an aromatic compound comprising one electrophilic group and one nucleophilic group can also be reacted all together. Typically, in this invented method, an aromatic diol, such as a hydroquinone and/or a bisphenol, undergoes a condensation reaction with an aromatic dihalocompound, or an aromatic monohydroxy-monohalocompound undergoes an auto-condensation reaction; an aromatic diol, an aromatic dihalocompound and an aromatic monohydroxy-monohalocompound can also be reacted all together to form the PAEK.

Aromatic dinucleophiles for use in the present invention are usually chosen from aromatic diols, wherein each of the hydroxy groups (—OH) is directly linked to a carbon atom of a benzenic ring. Both hydroxy groups may be directly linked to different carbon atoms of the same benzenic ring, or to carbon atoms of different benzenic rings. In certain embodiments, the hydroxy groups are in para position with respect to each other.

Certain aromatic dinucleophiles useful in the synthesis of PAEKs in accordance with the present invention are aromatic diols selected from the group consisting of:

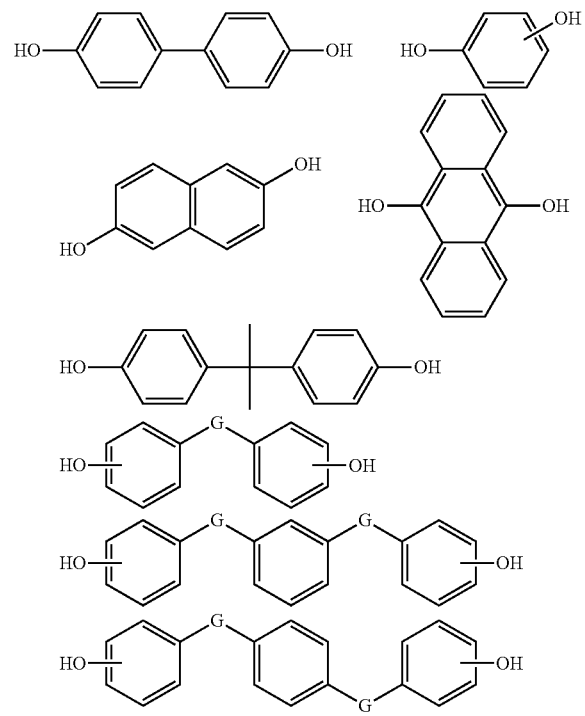

and any combinations thereof, wherein G is independently selected from a carbonyl group (C=O), an oxygen atom (—O—) or a sulfur atom (—S—); in particular, in the last two depicted formulae, all the G may be oxygen atoms.

Preferred aromatic dinucleophiles for use in the present invention are chosen from p-hydroquinone, 4,4'-dihydroxybenzophenone, 4,4'-biphenol, 1,4-bis-(p-hydroxybenzoyl)benzene and 1,3-bis-(p-hydroxybenzoyl)benzene, and any combination thereof. More preferably, the aromatic dinucleophiles are chosen from p-hydroquinone, 4,4'-dihydroxybenzophenone and any combinations thereof. Still more preferably, the aromatic dinucleophile is p-hydroquinone.

Aromatic electrophiles for use in the present invention are usually chosen from aromatic dihalocompounds, wherein each of the halogeno groups is directly linked to a carbon atom of a benzenic ring; both halogeno groups may be directly linked to different carbon atoms of the same benzenic ring or to carbon atoms of different benzenic rings. In certain embodiments, the halogeno groups are in para position with respect to each other.

Certain aromatic dielectrophiles useful in the synthesis of PAEKs in accordance with the present invention are aromatic dihalocompounds selected from the group consisting of 4,4'-halobenzophenone, 1,4-bis(p-halobenzoyl)benzene, 1,3-bis(p-halobenzoyl)benzene 1,4-bis(p-halobenzoyl)biphenyl, and any combinations thereof. Aromatic electrophiles for use in the present invention are preferably chosen from 4,4'-difluorobenzophenone, 1,4-bis(p-fluorobenzoyl)benzene, 1,3-bis(p-fluorobenzoyl)benzene 1,4-bis(p-fluorobenzoyl)biphenyl, and any combinations thereof. More preferably, the aromatic dielectrophile is 4,4'-difluorobenzophenone. Precisely, the Applicant has surprisingly found that, when 4,4'-difluorobenzophenone is the aromatic dielectrophile, improved results are obtained when said 4,4'-difluorobenzophenone complies with certain impurity limitations.

Embodiment (D)

Hence, in a particular embodiment (D) of the present invention, the invented method for the preparation of a poly(aryletherketone) is a method by aromatic nucleophilic substitution in the presence of particulate sodium carbonate having the particle size distribution requirements as described in the present document, said method comprising the condensation reaction between an aromatic dinucleophile and 4,4'-difluorobenzophenone, wherein the 4,4'-difluorobenzophenone meets the following impurity limitation: [2,4'-difluorobenzophenone]+[4-monofluorobenzophenone] ≤1250 ppm wherein the amounts of 2,4'-difluorobenzophenone and 4-monofluorobenzophenone in 4,4'-difluorobenzophenone are determined by liquid chromatography analysis.

For example, the liquid chromatography determination can be carried out with a Agilent 1100 LC High Pressure Liquid Chromatography instrument using a Supelco Discovery HS F5, 5 μm, 25 cm×4.6 mm column. Suitable analysis conditions include:

Mobile Phase: acetonitrile/deionized water
Gradient: 60/40 acetonitrile/water for 5 minutes, increase to 100% acetonitrile in a further 10 minutes.
Flow rate: 1 ml/minute
Detection: UV 254 nm
Temperature: 50° C.
Injection Volume: 5 μl The sample is prepared by dissolving about 0.01 g of 4,4'-difluorobenzophenone in 100 ml of acetone.

The amount of 2,4'-difluorobenzophenone and 4-monofluorobenzophenone in 4,4'-difluorobenzophenone is typically determined using a calibration with three external standards of these commercially available compounds, of different concentrations, to generate a calibration curve.

Under the above detailed conditions, the retention time of 2,4'-DFBP is typically about 7.4 minutes and 7.1 minutes for 4-monofluorobenzophenone. The retention time for 4,4'-DFBP is typically about 7.7 minutes.

Results are expressed as parts per million of the two impurities.

In present embodiment (D), preferably, the 4,4'-difluorobenzophenone further meets the following impurity limitation:
[2,4'-difluorobenzophenone]≤750 ppm,
and, more preferably, it further meets at least one of the following sets of impurity limitations:
Set 1: [2,4'-difluorobenzophenone]≤750 ppm, and [4-monofluorobenzophenone]≤500 ppm, Set 2: [2,4'-difluorobenzophenone]≤300 ppm, and [4-monofluorobenzophenone]≤950 ppm.

Aromatic compounds comprising one electrophilic group and one nucleophilic group for use in the present invention are usually chosen from aromatic monohydroxy-monohalocompounds compounds, wherein the hydroxy group is directly linked to a carbon atom of a benzenic ring and the halogeno group is also directly linked to a carbon atom of a benzenic ring; both groups may be linked to different carbon atoms of the same benzenic ring or to carbon atoms of different benzenic rings. In certain embodiments, the hydroxy group is in para position with respect to the halogeno group.

Certain aromatic useful in the synthesis of PAEKs in accordance with the present invention are aromatic monohydroxy-monohalocompounds selected from the group consisting of: 4-halo-4'-hydroxybenzophenone, 4-(p-halobenzoyl)-4'-hydroxybiphenyl, 4-(p-halobenzoyl)-4'-hydroxydiphenyl ether, 4-halo-4''-hydroxyterephthalophenone, 4-halo-4'-hydroxyisophthalophenone; and any combinations thereof. Preferred aromatic monohydroxy-monohalocompounds are preferably selected from the group consisting of: 4-fluoro-4'-hydroxybenzophenone, 4-(p-fluorobenzoyl)-4'-hydroxybiphenyl, 4-(p-fluorobenzoyl)-4'-hydroxydiphenyl ether, 4-fluoro-4''-hydroxyterephthalophenone, 4-halo-4'-hydroxyisophthalophenone; and any combinations thereof. More preferably, the aromatic monohydroxy-monohalocompound is 4-fluoro-4'-hydroxybenzophenone.

In accordance with the method of the present invention, the poly(aryl ether ketone) (PAEK) is generally produced in a solvent. Such PAEK reactions by aromatic nucleophilic substitution are often carried out in a solvent that often is, or that often contains, diphenylsulfone. However, many other solvents can be used, including benzophenone, dibenzothiophene dioxide, etc. When the solvent is or contains diphenylsulfone, said diphenylsulfone meets advantageously one or more impurity limitations, as specified in embodiment (E) hereinafter.

Embodiment (E)

In a preferred embodiment (E) of the present invention, the invented method for the preparation of a poly(aryletherketone) is a method by aromatic nucleophilic substitution in the presence of particulate sodium carbonate having the particle size distribution requirements as described in the present document, in a solvent comprising a diphenylsulfone, wherein said diphenylsulfone meets at least one of the following impurity limitations:

| | |
|---|---|
| Monomethyldiphenylsulfone content (sum of all isomers) | Less than 0.2 area % |
| Monochlorodiphenylsulfone content (sum of all isomers) | Less than 0.08 area % |
| Sodium content | Less than 55 ppm |
| Potassium content | Less than 15 ppm |
| Iron content | Less than 5 ppm |
| Residual acidity content | Less than 2.0 μeq/g |
| Diphenylsulfide content | Less than 2.0 wt. % |
| APHA of 20 wt. % solution in acetone at 25° C. | Less than 50 |
| Total chlorine content | Less than 120 ppm | where ppm and wt. % are based on the total weight of the diphenylsulfone and area % represents the ratio of the GC peak area of the impurity of concern over the total area of all GC peaks of the diphenylsulfone.

The residual acidity content in diphenylsulfone can be determined as follows. Approximately 3 g of diphenylsulfone sample is weighed to the nearest 0.1 mg and added to an empty glass titration vessel. 55 ml of high-purity methylene chloride is added, followed by addition of a 5.00 ml aliquot of spiking solution, which contains six drops of 37% hydrochloric acid per liter, into the same titration vessel. The vessel is then attached to the titrator cell assembly containing the buret tip, pH electrode, and magnetic stirrer. The vessel is then purged with carbon dioxide free nitrogen for 5-7 minutes. While continuing the nitrogen purge, the vessel contents is titrated with 0.025 N tetrabutylammonium hydroxide in 1:12 methanol:toluene and the volume of titrant required to reach the strong acid endpoint is measured. A blank titration is performed using the same parameters, except that the sample was omitted. Results are calculated using the following equation:

$$\text{Acidity} = ((VS1 - VB1) * N * 100000)/W \text{ in microequivalents per gram of sample}$$

where VS1 is the amount of titrant in ml required to reach the strong acid/base equivalence points when sample solution is titrated and VB1 is the amount of titrant in ml required to reach the strong acid/base equivalence point when only the blank solution is titrated, W is the sample weight, and N is the normality of the tetrabutylammonium hydroxide titrant. If acidity is negative, the sample contains basic species.

The sodium, potassium, and iron content in diphenylsulfone can be determined as follows. Concentrations of sodium, potassium, and iron are measured in diphenylsulfone by ashing of the sample followed by measurement of element concentration by inductively-coupled plasma atomic emission spectrometry. Approximately 3 g of diphenylsulfone sample is weighed into platinum crucibles using an analytical balance. Two drops of concentrated, trace metals grade sulfuric acid is added to each sample and the crucibles are placed into a muffle furnace set to 250° C. After the diphenylsulfone has vaporized, the furnace temperature is raised to 525° C. for 1 hour to remove any organic residues. Metallic residues are dissolved by adding 1 ml of concentrated hydrochloric acid to the crucible and warming at 50° C. to dissolve the ash. After addition of 5 ml of deionized water and additional warming, crucible contents are quantitatively transferred to a 25-ml volumetric flask, diluted to the mark with deionized water, and mixed well. The diluted solutions are then analyzed by ICP-AES against standards made from certified sodium, potassium, and iron standard solutions. Emission is monitored at the following wavelengths for the elements of interest: sodium: 589.592 nm, potassium: 766.490 nm and iron: 238.204 nm. Plasma conditions used for the analysis are: plasma input power: 1300 watts, plasma argon flow: 15 liters per minute, auxiliary argon flow: 0.5 liters per minute, nebulizer flow: 1.2 liters per minute, and sample flow rate: 1.5 milliliters per minute. Element concentrations in the samples are calculated by the ICP operating software from the element emission line intensities.

The total chlorine content in diphenylsulfone can be determined as follows. Using forceps, a clean, dry combustion boat is placed onto a microbalance, and the balance is zeroed. 1 mg of diphenylsulfone sample is weighed into the boat and weight is recorded to 0.001 mg. The combustion boat and sample are placed in the introduction port of a Thermo Electron Corporation ECS 1200 Halogen Analyzer, and the port is capped. The sample weight is entered into the sample weight field on the instrument computer. The sample analysis cycle is then started. The sample is burned in a mixture of argon and oxygen and the combustion products are carried by the combustion gas stream into a titration cell. Hydrogen chloride produced from the combustion is absorbed into the cell solution from the gas stream, and is coulometrically titrated with silver ions. Total chlorine content is displayed at the end of the titration.

The diphenylsulfide content in diphenylsulfone can be determined by liquid chromatography, as explained hereinafter. HPLC analysis is carried out on a Waters Alliance 2795 LC instrument using a Supelco Discovery HS F5 25 cm×4.6 mm column. The analysis conditions are:

Mobile phase: acetonitrile/deionized water.
Gradient: 60/40 acetonitrile/water, hold for 5 minutes, increase to 100% acetonitrile in further 10 minutes, hold for 5 minutes at 100% acetonitrile
Flow rate: 1 ml/minute
Injection volume: 10 μl
Detection: UV at 254 nm The sample is prepared by dissolving 0.2 g of diphenylsulfone (DPS) in 10 g of acetonitrile. The concentration of diphenylsulfide is determined using a low concentration diphenylsulfide as an external calibration standard (commercially available). The retention time for DPS is typically 6.2 minutes and the retention time for diphenylsulfide is typically 10.7 minutes. The diphenylsulfide concentration in the DPS sample is assessed by the area of the diphenylsulfide peak/total peak area of DPS plus impurities.

The monochlorodiphenylsulfone and monomethyldiphenylsulfone content in diphenylsulfone can be determined by gas chromatography, as explained hereinafter. GC analysis is performed on an HP5890 series 11 gas chromatograph using a Restek RTx-5MS, 15 m×0.25 mm internal diameter×0.25 μm film thickness column. The following GC conditions are used:

Helium flow rate: 1 ml/minute,
Injector temperature: 250° C.
FID temperature: 250° C.
Oven Temperature Program: 100° C., hold 1 minute, 30° C./minute to 250° C., hold 1 minute
Total run time: 14 minutes
Injection volume: 1 μl
Split 40:1

The sample is prepared by dissolving 0.2 g of DPS in 5 ml of acetone. Typically the GC retention times for monomethyldiphenylsulfone isomers are 8.0 and 8.1 minutes and for monochlorodiphenylsulfone 8.2 minutes. The identity of the impurities is determined by GCMS run on the sample solution. The impurity concentrations are quoted as area %, calculated from GC FID peak areas. When several isomers are present, the concentration includes the sum of these isomers.

The color (APHA) of DPS in acetone can be determined as follows. 20 g of diphenylsulfone are dissolved in 80 g of acetone at 25° C. The acetone used contains less than 0.5 wt. % water. Color of the solution is measured as compared to Pt—Co standards in the APHA scale (ASTM D1209-00), using a Gretag Macbeth Color Eye Ci5 Spectrophotometer for the comparison. The blank used is distilled water.

In the method in accordance with embodiment (E) of the present invention, said diphenylsulfone meets preferably the impurity limitations for monomethyldiphenylsulfone, monochlorodiphenylsulfone, and residual acidity.

Additionally or alternatively, in the method in accordance with embodiment (E) of the present invention, said diphenylsulfone meets preferably the impurity limitations for sodium, iron, diphenylsulfide, and APHA of 20 wt. % solution in acetone at 25° C.

In the method in accordance with embodiment (E) of the present invention, excellent results were obtained when all the impurity limitations as above recited were met.

As above said, in accordance with the method of the present invention, the poly(aryl ether ketone) (PAEK) is generally produced in a solvent. Additionally, such PAEK reactions by aromatic nucleophilic substitution may be carried out in the additional presence of a cosolvent which forms an azeotrope with water, to help the removal of water from the reaction mixture, such as p-xylene, chlorobenzene or toluene. In a particular embodiment of the present invention, the poly(aryl ether ketone) is produced in a solvent and in the absence of p-xylene. In another particular embodiment of the present invention, the poly(aryl ether ketone) is produced in a solvent and in the absence of any cosolvent which forms an azeotrope with water.

As already mentioned, the present invention relates, in part, to a method for the preparation of a poly(aryl ether ketone) by aromatic nucleophilic substitution in the presence of particulate sodium carbonate, wherein said particulate sodium carbonate has a particle size distribution as follows: $D_{90} \geq 45$ μm and $D_{90} \leq 250$ μm and $D_{99.5} \leq 710$ μm, and to the poly(aryl ether ketone) produced by said method.

As used herein, a sodium carbonate particle size distribution expressed as $D_{xx} \leq Y$ μm refers to the percentage (xx %) of sodium carbonate particles by weight in a sample that are less than or equal to Y μm in diameter, as measured usually by mechanical sieving, typically as described in the examples (see hereinafter: "EXAMPLES" Section—"Particle size distribution (PSD) of $Na_2CO_3$ determined by mechanical sieving").

On one hand, $Na_2CO_3$ that is "too fine" is to be avoided as it can notably lead to a low bulk density product that is difficult to handle and synthesis reaction kinetics that are difficult to control. With this regard, the Applicant found that $Na_2CO_3$ with a $D_{90} \geq 45$ μm was required.

On the other hand, $Na_2CO_3$ that contains a certain amount of "big" particles, and especially of "very big" particles (i.e., typically of about 710 μm or more), is also to be avoided as it can notably slow down the polymerization rate, or require the use of an undesirably high amount of $K_2CO_3$ or other higher alkali metal carbonate (at fixed $Na_2CO_3$ amount); $Na_2CO_3$ that contains a certain amount of "big" particles, and especially of "very big" particles, can also result in polymerizations having poor kinetics consistency. With this regard, the Applicant found that $Na_2CO_3$ with a $D_{90} \leq 250$ μm and with a $D_{99.5} \leq 710$ μm was also required.

The use of particulate sodium carbonate meeting the invention particle size specifications provides several benefits, including the ability to synthesize PAEKs in the absence of a cosolvent forming an azeotrope with water such as p-xylene, and thereby prepare PAEKs with no trace of residual cosolvent (such cosolvents, like p-xylene, are generally toxic). Cosolvents forming an azeotrope with water used in the synthesis of PAEK resins are known to those of skill in the art, and in addition to p-xylene include chlorobenzene, toluene, etc.

The use of particulate sodium carbonate meeting the invention particle size specifications makes it also possible to manufacture lower color, whiter PAEK resins.

The use of particulate sodium carbonate meeting the invention particle size specifications results also beneficially in improved kinetics consistency.

The invention particle size limitation $D_{99.5} \leq 710$ μm includes, of course, $D_{99.5}$ values of: $D_{99.5} \leq 700$ μm, $D_{99.5} \leq 650$ μm, $D_{99.5} \leq 600$ μm, $D_{99.5} \leq 550$ μm, $D_{99.5} \leq 500$ μm, $D_{99.5} \leq 450$ μm, $D_{99.5} \leq 400$ μm, $D_{99.5} \leq 350$ μm, $D_{99.5} \leq 300$ μm, $D_{99.5} \leq 250$ μm, $D_{99.5} \leq 224$ μm, $D_{99.5} \leq 200$ μm, $D_{99.5} \leq 150$ μm, etc. In this regard, where a numerical limit is stated, all values and subranges within the limit are specifically included as if explicitly written out. Preferably, the $D_{99.5}$ of the sodium carbonate particles according to the invention is of at most 630 μm; more preferably, it is of at most 500 μm; still more preferably, it is of at most 425 μm; most preferably, it is of at most 355 μm.

The lower limit of the $D_{99.5}$ of the sodium carbonate particles according to the invention is not critical. Obviously, it is of at least 45 μm, and may be notably of at least 63 μm, at least 75 μm, at least 90 μm, at least 100 μm, at least 125 μm or at least 150 μm.

The invention particle size limitation $D_{90} \leq 45$ μm includes, of course, $D_{90}$ values of: $D_{90} \geq 75$ μm, $D_{90} \geq 100$ μm, $D_{90} \geq 125$ μm, $D_{90} \geq 150$ μm, $D_{90} \geq 175$ μm, $D_{90} \geq 200$ μm, etc. In this regard, where a numerical limit is stated, all values and subranges within the limit are specifically included as if explicitly written out. Preferably, the $D_{90}$ of the sodium carbonate particles according to the invention is of at least 63 μm; more preferably, it is of at least 90 μm; still more preferably, it is of at least 112 μm.

The invention particle size limitation $D_{90} \leq 250$ μm includes, of course, $D_{90}$ values of: $D_{90} \leq 200$ μm, $D_{90} \leq 150$ μm, $D_{99.5} \leq 100$ μm, etc. In this regard, where a numerical limit is stated, all values and subranges within the limit are specifically included as if explicitly written out. Preferably, the $D_{90}$ of the sodium carbonate particles is of at most 212 μm; more preferably, it is of at most 180 μm; still more preferably, it is of at most 150 μm.

In preferred embodiments of the invention the sodium carbonate has the following particle size distributions:

$D_{99.5} \leq 630$ μm, $D_{90} \leq 212$ μm, and $D_{90} \geq 45$ μm; or
$D_{99.5} \leq 500$ μm, $D_{90} \leq 212$ μm, and $D_{90} \geq 45$ μm; or
$D_{99.5} \leq 425$ μm, $D_{90} \leq 212$ μm, and $D_{90} \geq 45$ μm; or
$D_{99.5} \leq 630$ μm, $D_{90} \leq 180$ μm, and $D_{90} \geq 45$ μm; or
$D_{99.5} \leq 500$ μM, $D_{90} \leq 180$ μm, and $D_{90} \geq 45$ μm; or
$D_{99.5} \leq 425$ μm, $D_{90} \leq 180$ μm, and $D_{90} \geq 45$ μm; or
$D_{99.5} \leq 630$ μm, $D_{90} \leq 212$ μm, and $D_{90} \geq 63$ μm; or
$D_{99.5} \leq 500$ μm, $D_{90} \leq 212$ μm, and $D_{90} \geq 63$ μm; or
$D_{99.5} \leq 425$ μm, $D_{90} \leq 212$ μm, and $D_{90} \geq 63$ μm; or
$D_{99.5} \leq 630$ μm, $D_{90} \leq 212$ μm, and $D_{90} \geq 90$ μm; or
$D_{99.5} \leq 500$ μm, $D_{90} \leq 212$ μm, and $D_{90} \geq 90$ μm; or
$D_{99.5} \leq 425$ μm, $D_{90} \leq 212$ μm, and $D_{90} \geq 90$ μm.

The particle size distribution of the sodium carbonate can be determined by any appropriate means. Among others, it can be notably cited Dynamic Light Scattering (DLS) and mechanical sieving. However, for easiness, broad availability and excellent repeatability, preference is given to mechanical sieving. The analysis is typically based on the mechanical separation of the various fractions on a series of superimposed sieves. The analysis can be made in full accordance with ASTM E 359-00 (reapproved 2005)$^{\epsilon 1}$, the whole content of which being herein incorporated by reference; ASTM E 359-00 (reapproved 2005)$^{\epsilon 1}$ concerns various measurements made specifically on sodium carbonate, notably sieve analysis. Alternatively, the analysis can include certain but not all the requirements set forth in ASTM E 359-00 (reapproved 2005)$^{\epsilon 1}$; for example, the analysis can include all the requirements set forth in ASTM E 359-00 ASTM E 359-00, except using a different set of sieves. The particle size distribution is advantageously determined with an automatic mechanical sieving device, such Ro-Tap RX-29 sieve shaker (as commercialized by W. S. Tyler Company). Said automatic mechanical sieving device comprises means for mounting nested, screen-bottomed pans in a frame. The mounting frame is provided with translational motion means at one end and circular motion means at the other to provide continual movement of particles on the sieves. The device is thus able to transmit combined movements in the horizontal plane and shocks along the vertical axis to a pile of superimposed sieves. The device is advantageously set with a fixed number of horizontal revolutions and taps per minute. Also, the sieves mounted on the sieve shaker are advantageously in conformity with standard ISO 3310-1 or ASTM E-11, preferably with wire stainless steel circular sieves with square meshes, metal mounting with a diameter 200 mm. The device and its sieves are advantageously checked periodically using a reference powder; the control frequency should be desirably be as high as possible for early detection of any deviation, as possibly resulting for damaged meshes. The sieves are superimposed and assembled from top to bottom by descending order of opening mesh. A fixed weight amount of the powder to be investigated is weighed with an analytical balance and placed on top of the widest sieve. By vibrating the sieving machine, the powder material is conveyed through the various sieves. The sieving operation is run for a fixed amount of time. The residues on the sieves are weighed with an analytical balance and related mathematically to the initial weight of material. Notably $D_{50}$, $D_{90}$, and $D_{99.5}$ values can be calculated from the residues weights. This calculation is generally made as follows:

1) Calculate the weight percentage of the test specimen retained on each sieve.
2) Express the weight percentage passing through each sieve, and cumulated.

For example, with the set of sieves as described in the "EXAMPLES" section of the present application, the cumulative percent retained on the 250 μm sieve can determined by adding the weights of the particles on the 1000, 500 and 250 μm, dividing the sum by the total weight of the original sample and multiplying by 100. The results can be displayed on a graph were the Y-coordinate represents the cumulative weight percent particles retained on a particular sieve. The X-coordinate corresponds to sieve size. The Y-value for a particular sieve can be determined by adding the weight of the particles retained on that sieve plus the weights of the particles retained on all larger sieves above it and dividing the sum by the total weight of the sample.

In more general terms, a total of n sieves (wherein n is a positive integer generally equal to at least 5, preferably of at least 8, when the whole particle size distribution is to be measured) of nominal aperture size $x_i$ (wherein i=1 to n) are ranked in order of increasing size, i.e. $x_{i+1}$ is larger than $x_i$.

The nominal aperture sizes of the sieves form advantageously a geometric progression (thus, $x_{i+1} = k \cdot x_i$ for i=1 to n−1, wherein k is a constant); as common choices for the "k" constant, it can be cited 2, $2^{0.5}$ (1.4142) and $2^{0.25}$ (1.1892).

The sieves may be ISO 3310-1 or ASTM E-11 test sieves having a diameter of 200 mm, as notably commercialized by LAVAL LAB Inc. These ones are generally characterized by:
 insofar as their full height is concerned: overall height of 65 mm, and depth to cloth of 50 mm;
 concerning insofar has their half height is concerned: overall height of 40 mm, and depth to cloth of 25 mm.

They can be constructed notably with a brass frame and a stainless steel cloth, or with a stainless steel frame and a stainless steel cloth.

Certain suitable sets of sieves are composed of eight or ten ISO 3310-1 or ASTM E-11 test sieves having a diameter of 200 mm, having the following aperture size or ASTM opening designation:

2000 μm (ASTM No. 10), 1000 μm (ASTM No. 18), 500 μm (ASTM No. 35), 250 μm (ASTM No. 60), 125 μm (ASTM No. 120), 90 μm (ASTM No. 170), 63 μm (ASTM No. 230) and 45 μm (ASTM No. 325);

1000 μm (ASTM No. 18), 500 μm (ASTM No. 35), 250 μm (ASTM No. 60), 180 μm (ASTM No. 80), 125 μm (ASTM (No. 120), 90 μm (ASTM No. 170), 63 μm (ASTM No. 230) and 45 μm (ASTM No. 325);

1000 μm (ASTM No. 18), 710 μm (ASTM No. 25), 500 μm (ASTM No. 35), 355 μm (ASTM No. 45), 250 μm (ASTM No. 60), 180 μm (ASTM No. 80), 125 μm (ASTM (No. 120), 90 μm (ASTM No. 170), 63 μm (ASTM No. 230) and 45 μm (ASTM No. 325); and 850 μm (ASTM No. 20), 600 μm (ASTM No. 30), 425 μm (ASTM No. 40), 300 μm (ASTM No. 50), 212 μm (ASTM No. 70), 150 μm (ASTM No. 100), 106 μm (ASTM (No. 140), 75 μm (ASTM No. 200), 53 μm (ASTM No. 270) and 38 μm (ASTM No. 400).

The sieves of the last two above sets are characterized by a k-constant equal the square root of 2.

At the end of the sieving analysis, the weight fraction caught on each screen is calculated. $\Phi_i$, the fraction on sieve i, of size $x_i$, is thus:

$$\phi_i = \frac{w_i}{\sum_{i=1}^{n} w_i}$$

wherein $w_i$ is the weight of powder collected on sieve i sample weight

The percentage under the size $x_t$ $P_t$ is thus defined as:

$$P_t = \sum_{i=1}^{t-1} \phi_i$$

To obtain the cumulative curve, $P_t$, the percentage under the size $x_t$ is plotted versus $x_t$. The curve can be built by considering in each point the following slope:

$$\left(\frac{dP}{dx}\right)_{x=x_t} = \frac{\phi_t}{x_{t+1} - x_t}$$

3) Determine $D_z$ values (0<z<100), e.g. determine $D_{50}$, $D_{90}$ and $D_{99.5}$.

$D_z$ is defined as the abscissa of the curve for P=z/100, i.e. z wt. % of the sample is under the size of $D_z$.

$D_{50}$ is defined as the abscissa of the curve for P=0.50, i.e. 50 wt. % of the sample is under the size of $D_{50}$.

$D_{90}$ is defined as the abscissa of the curve for P=0.90, i.e. 90 wt. % of the sample is under the size of $D_{90}$.

$D_{99.5}$ is defined as the abscissa of the curve for P=0.995, i.e. 99.5 wt. % of the sample is under the size of $D_{99.5}$.

Two or more sieving measurements can also be made on a same sample using different sets of sieves, e.g. a first sieving operation (for the characterization of the bigger particles/determination of the $D_{99.5}$) can be made using the eight following ISO 3310-1 or ASTM E-11 test sieves having a diameter of 200 mm:

(set I) 1000 μm (ASTM No. 18), 850 μm (ASTM No. 20),
710 μm (ASTM No. 25), 600 μm (ASTM No. 30),
500 μm (ASTM No. 35), 425 μm (ASTM No. 40),
355 μm (ASTM No. 45), 300 μm (ASTM No. 50)

while another sieving operation (for the characterization of the finer particles/determination of the $D_{90}$) can be made using these ten other ISO 3310-1 or ASTM E-11 test sieves having a diameter of 200 mm:

(set II) 250 μm (ASTM No. 60), 212 μm (ASTM No. 70),
150 μm (ASTM No. 100), 125 μm (ASTM No. 120),
106 μm (ASTM (No. 140), 90 μm (ASTM No. 170),
75 μm (ASTM No. 200), 63 μm (ASTM No. 230),
53 μm (ASTM No. 270), 45 μm (ASTM No. 325).

The particle size distribution of the sodium carbonate used in the method for preparing PEEK in accordance with the present invention is advantageously determined on a sample which is representative of the whole sodium carbonate which is used in said method. For the purpose of the present invention, a representative sample can be defined as a sample of which at least the $D_{90}$ and $D_{99.5}$ values are essentially identical, if not identical, to the ones of the whole sodium carbonate which is used in said method. To achieve appropriate sampling, the skilled person will advantageously rely upon all those sampling recommendations which do form part of the general knowledge and are broadly described in various encyclopedias, including but not limited to "Sampling", Reg. Davies, in "Kirk-Othmer Encyclopedia of Chemical Technology", online Ed. 2000, the whole content of which is herein incorporated by reference. Since sodium carbonate can be viewed as a free-flowing powder, sampling procedures suitable for stored free-flowing powders will be used preferably. For sodium carbonate stored in bags, the use of a thief sampler to sample different parts of the bag is generally preferred; the particle size analysis is then conducted on a composite sample. For small containers (e.g. 500 g reagent jar), it is typically preferred that the container be thoroughly shaken and several (3 or more) samples be scooped out of it; a composite sample is then used for the particle size analysis. Provided the particle size distribution of the carbonate is not affected by subsequent packaging, transporting and/or storing operations, it may be convenient to proceed with the sampling "at-line" directly at the production site on flowing streams of the powder, by extracting from the product stream by the projection of a sample tube into the flow.

In another preferred embodiment the sodium carbonate is anhydrous. However, the sodium carbonate does not need to be dry since situations occur where, e.g., at the temperature at which the intended reaction is run, any moisture would be driven off. It is typically very important to measure the moisture content of the $Na_2CO_3$ before use to ensure accurate stoichiometry. If $Na_2CO_3$ contains too much moisture (>3-5 wt. %), it can lump and the particle size requirement may not be met.

Sodium carbonate is broadly commercially available, either in the form of dense sodium carbonate or light sodium carbonate.

Light sodium carbonate, also called light soda ash, has generally a free flowing density, as measured in accordance with ISO 903 standard, of between 0.48 kg/dm$^3$ and 0.65 kg/dm$^3$; often, the free flowing density of light sodium carbonate is from 0.50 kg/dm$^3$ to 0.60 kg/dm$^3$, with typical values in the range of from 0.53 kg/dm$^3$ to 0.57 kg/dm$^3$. In general, light sodium carbonate is chemically synthesized by the SOLVAY® process, also referred to as the "ammonia-soda process". This one was developed into its modern form by Ernest Solvay during the 1860s, and has been thoroughly described in the scientific literature. The overall process reaction scheme is:

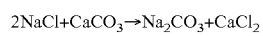
$2NaCl + CaCO_3 \rightarrow Na_2CO_3 + CaCl_2$

The actual implementation of this global, overall reaction is intricate. The process comprises a step wherein carbon dioxide ($CO_2$) passes through a usually concentrated aqueous solution of sodium chloride (NaCl) and ammonia (NH$_3$); a sodium bicarbonate (NaHCO$_3$) precipitate is obtained, in accordance with the following reaction scheme:

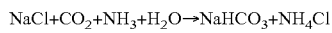
$$NaCl+CO_2+NH_3+H_2O \rightarrow NaHCO_3+NH_4Cl$$

It comprises also a step, subsequent to the previously described one, wherein the sodium bicarbonate (NaHCO$_3$) precipitate is converted to the final product, sodium carbonate (Na$_2$CO$_3$), by calcination (usually at a temperature from 160° C. to 230° C.), producing water and carbon dioxide as by-products:

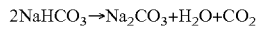
$$2NaHCO_3 \rightarrow Na_2CO_3+H_2O+CO_2$$

The elimination of water from the particles during the calcination step, creates an important porosity in the particles without substantially modifying their particle size distribution, resulting thereby in a product having a free flowing density about twice lower than the density of non porous particles. Said light sodium carbonate has generally a particle size distribution characterized by a $D_{90} \geq 45$ µm; besides, the $D_{50}$ of the particle size distribution ranges generally from about 25 µm to about 150 µm, and is often between 30 µm and 100 µm.

Additional details of the industrial implementation of this process can be found notably at "http://en.wikipedia.org/wiki/Solvay_process".

Dense sodium carbonate, commonly called dense soda ash, has generally a free flowing density, as measured in accordance with ISO 903 standard, of from 0.90 kg/dm$^3$ to 1.20 kg/dm$^3$. Dense sodium carbonate may be prepared notably by calcinating trona or by re-crystallizing light soda carbonate as be obtained by the above detailed SOLVAY® process.

In general, neither the commercially available dense sodium carbonates nor the commercially available light sodium carbonates have a particle size distribution as required the present invention. Indeed, values well above 1,000 µm are commonly reported by the manufacturers as typical values for the $D_{99.5}$ of the commercially available dense sodium carbonates, while typical values of not less than 1,000 µm are commonly reported in case of commercially available light sodium carbonates, i.e. in both cases, these typical values are well above the upper limit specified for the $D_{99.5}$ of the sodium carbonate in accordance with the present invention. Besides, typical values for the $D_{90}$ of the commercially available dense sodium carbonates are commonly reported to be well above 500 µm, i.e. also well above the specified upper limit for the $D_{90}$ of the sodium carbonate in accordance with the present invention. It can be finally noted that ground sodium carbonates are not broadly commercially available and have generally a $D_{90}$ well below 45 µm.

Yet, as will explained below, it is easy for the skilled person, searching for obtaining a sodium carbonate with the appropriate particle size requirements, to obtain it.

Dense sodium carbonates having the appropriate particle size requirements can be notably obtained by appropriate grinding and/or sieving dense sodium carbonates having a particle size distribution not in accordance with the present invention. Insofar as dense sodium carbonates are concerned, methods including at least one grinding step followed by at least one sieving step are preferred. As possibly suitable grinders, it can be notably cited jet mills such as helical jet mills, oval tube jet mills, counterjet mills, fluidized bed jet mills, and ball and plate jet mills, notably can be used. As possibly suitable sieves, it can be notably cited 710 µm, 630 µm, 500 µm, 400 µm, 300 µm, 250 µm, 200 µm, 150 µm and 125 µm sieves.

Light sodium carbonates having the appropriate particle size requirements can also be obtained by appropriate grinding and/or sieving light sodium carbonates having a particle size distribution not in accordance with the present invention. However, insofar as light sodium carbonates are concerned:
methods free of any grinding step are preferred for easiness; such methods may include a sieving step or not;
still for easiness, methods free of any grinding step and which are either free of any sieving step or which include a sieving step wherein light sodium carbonate particles are screened through a sieve having meshes of at least about 2 mm (length)×at least about 2 mm (width) are much preferred; methods free of any grinding step and which are either free of any sieving step or which include a sieving step wherein light sodium carbonate particles are screened through a sieve having meshes of at least 5 mm×at least about 5 mm, are still more preferred; excellent results were obtained with methods including a sieving step wherein light sodium particles are screened through a sieve having meshes of at least 8 mm×at least about 8 mm. The light sodium carbonate particles possibly subject to the sieving step are typically those synthesized by the SOLVAY® process, after the sodium carbonate is formed by calcination from the sodium bicarbonate precipitate; the screened light sodium carbonate particles represent generally the final product either having the final particle size distribution, or having essentially the final particle size distribution, or having substantially the final particle size distribution (wherein slight deviations of the particle size distribution may occur subsequently e.g. as the result of storing, packaging and transport operations).

A particularly preferred method for obtaining light sodium carbonates having the appropriate particle size requirements comprises selecting said light sodium carbonates among different lots of one or more grades of commercially available light sodium carbonates, as detailed below. As used herein, a lot designates a collection of light sodium carbonate particles which presents, at macroscopic scale, essentially homogeneous, if not homogeneous, set of properties; otherwise said, different samples extracted from a same lot in accordance with well-known good practice sampling rules, can be characterized by essentially the same, if not the same, $D_{90}$ and $D_{99.5}$ values. The Applicant determined the particle size distribution of numerous lots of commercially available (unground) light sodium carbonates from different sources, and observed that, among all these lots, none had a $D_{90}$ below 45 µm; as a matter of fact, their $D_{90}$ ranged usually from about 100 µm to about 250 µm, i.e. most of them complied with both requirements set forth for the $D_{90}$ in accordance with the present invention. Concerning the $D_{99.5}$ of the commercially available light sodium carbonates, the Applicant observed that its variability from one lot to another was surprisingly high, including when considering lots produced at relatively short intervals of time by the same manufacturer in the same plant; it deduced wisely therefrom that this variability could be exploited to its own benefit, because, among the lots produced, certain had the appropriate particle size requirements, while certain other lots of the same commercial grade had a $D_{99.5}$ above 710 µm, not in accordance with the present invention. Among the tested sodium carbonates, SODASOLVAY® L sodium carbonate, as produced notably in Dombasle or Rosignano plants, is particularly attractive because a rather high fraction of this commercial grade is formed by lots in accordance with the invention; thus, the Applicant could very easily identify appropriate lots for the polymerization method for preparing a PAEK in accordance with the present invention. Certain carefully selected lots of light sodium carbonates produced by other manufacturers like TIANJIN and BRUNNER MOND could also meet the particle size requirements as above expressed, and could thus also be suitably used in the polymerization method in accordance with the present invention. Thus, a method for providing a sodium carbonate which is especially well suited for the preparation of a poly(aryl ether ketone) by aromatic nucleophilic substitution, comprises:

chemically synthesizing a light sodium carbonate;
identifying among the light sodium carbonate at least one lot having a particle size distribution as follows:
$D_{90} \geq 45$ μm and $D_{90} \leq 250$ μm and $D_{99.5} \leq 710$ μm;
differentiating the lot from the rest of the light sodium carbonate;
providing at least part of the lot.

The identification of the light sodium carbonate having the appropriate particle size distribution can be made on-line, at-line or off-line, using any appropriate analytical determination means. Among them, it can notably be cited dynamic light scattering and sieving measurements. In practice, when sieving measurements are made, the use of only two sieves generally sufficient to get the needed information. Indeed, from the measurements made with a 710 μm-sieve and a 250-μm sieve, it can be checked whether the weight quantity which is refused on the 710 μm-sieve is ≤0.5% (corresponding to the $D_{99.5} \leq 710$ μm requirement) on one hand, and whether the weight quantity which is refused on the 250 μm-sieve is ≤10% (corresponding to the $D_{90} \leq 250$ μm requirement) on the other hand. As concerns the conformity with the last requirement ($D_{90} \geq 45$ μm), a 45 μm-sieve can further be used (the requirement is then proved to be met when the weight quantity passing through the 45 μm-sieve is ≤10%), but, since, in practice, essentially no or even no light sodium carbonate has naturally a $D_{90} \leq 45$ μm, this third determination is of utility, and can certainly be dropped once enough confidence is gained in the capability of the manufacture process of the light soda ash supplier.

The differentiation of the light sodium carbonate having the appropriate particle size distribution can be made by any appropriate differentiation means; it can include the marking of the lot, the tracing of the lot, the isolation of the lot, and any combination thereof.

Part of the lot, or the whole lot can be supplied notably to any distributor, any customer, and more generally to any user thereof. It is preferably used in the preparation of a poly(aryl ether ketone) by aromatic nucleophilic substitution.

In an exemplary method, the identification of the light sodium carbonate having the appropriate particle size distribution took place in a plant producing light sodium carbonate according to the SOLVAY® process. In the plant, the produced light sodium carbonate was packed into bags of 25 kg. The bags were stacked on pallets. Each pallett was composed of 50 bags, and was arbitrarily set to correspond to one lot of light sodium carbonate. In total, a high number of lots of 1 ton (commonly called "palletts" themselves) was prepared. Each pallette was characterized in that the light sodium carbonate contained in all its bag had been produced within a short interval of time; indeed, as it is common industrial practice, each pallette was formed individually, and the formation of a new pallette was only started after the previous one was completed. At least one every ten bags of each pallett was isolated, taking care of covering homegeneously the whole interval of time of the pallett of concern, i.e. at least 5 bags were isolated for each pallett. A sample of light sodium carbonate was taken of each bag, and its particle size distribution was measured by mechanical seaving as described in the Examples Section of the present document. A pallett was considered to have the appropriate particle size distribution only when each out of the at least 5 bag samples met the requirements. Using this method, it was observed that from about 10% to about 90% of the pallettes, typically about 50% of the pallettes, formed lots in accordance with the selection method of the present invention.

In certain preferred embodiments of the above method, the so-provided sodium carbonate complies with one or more of any of the particular features and/or preferences expressed for the sodium carbonate used in the method for preparing a poly(aryl ether ketone), as above detailed.

The present method for providing a sodium carbonate can be easily implemented, including at plant scale. It does not require any complex grinding and/or sieving operation, as required when a dense sodium carbonate is used as the starting material. Also, the so-provided sodium carbonate is cheap, as the result of its easiness of manufacture and its broad availability.

Related to the above, a particular aspect of the present invention concerns a method (M) for making the commerce of a light sodium carbonate, which comprises making publicly available, in any form and by any means, and/or providing to at least one customer, whatever bound to any confidentiality obligations or not, at least one information selected from the group consisting of:

the explicit information that the particle size distribution of the light sodium carbonate complies with the following sales specification:

$$D_{99.5} \leq D_{max,1} \text{ μm} \qquad (S1)$$

wherein $D_{max,1}$ can be any integer ≤710 μm;
the information (I1) from which it can be derived that the light sodium carbonate complies with the sale specification (S1);
the explicit information that the particle size distribution of the light sodium carbonate has the following typical value:

$$D_{99.5} = D_{max,4} \text{ μm} \qquad (S4)$$

wherein $D_{max,4}$ can be any integer ≤630 μm;
the information (I4) from which it can be derived that the light sodium carbonate has the typical value (S4), and any combination thereof.

Preferably, the method (M) further comprises making publicly available, in any form and by any means, and/or providing to at least one customer, whatever bound to any confidentiality obligations or not, at least one information selected from the group consisting of:

the explicit information that the particle size distribution of the light sodium carbonate complies with the following sales specification:

$$D_{90} \leq D_{max,2} \text{ μm} \qquad (S2)$$

wherein $D_{max,2}$ can be any integer ≤250 μm and $\leq D_{max,1}$;
the information (I2) from which it can be derived that the light sodium carbonate complies with the sales specification (S2);
the explicit information that the particle size distribution of the light sodium carbonate has the following typical value:

$$D_{90} = D_{max,5} \text{ μm} \qquad (S5)$$

wherein $D_{max,5}$ can be any integer $\leq 212$ μm and $\leq D_{max,4}$;
the information (I5) from which it can be derived that the light sodium carbonate has the typical (S5), and
any combination thereof
[preferred method (M)=(M')].

Still more preferably, the method (M) is the preferred method (M') as above described, which further comprises making publicly available, in any form and by any means, and/or providing to at least one customer, whatever bound to any confidentiality obligations or not, at least one of the following information:

the explicit information that the particle size distribution of the light sodium carbonate complies with the following sales specification:

$$D_{90} \geq D_{min,3} \text{ μm} \qquad (S3)$$

wherein $D_{min,3}$ can be integer $\geq 45$ μm and $\leq D_{max,2}$;
the information (I3) from which it can be derived that the light sodium carbonate complies with the sales specification (S3);
the explicit information that the particle size distribution of the light sodium carbonate has the following typical value:

$$D_{90} = D_{min,6} \text{ μm} \qquad (S6)$$

wherein $D_{min,6}$ can be any integer $\geq 63$ μm and $\leq D_{max,5}$;
the information (I6) from which it can be derived that the light sodium carbonate has the typical value (S6), and
any combination thereof
[very preferred method (M)=(M")].

For example, $D_{max,1}$ may be notably of at most 700 μm, at most 650 μm, at most 600 μm, at most 550 μm, at most 500 μm, at most 450 μm, at most 400 μm, at most 350 μm, at most 300 μm, at most 250 μm, at most 200 μm or at most 150 μm. Preferably, $D_{max,1}$ is of at most 630 μm; more preferably, it is of at most 500 μm; still more preferably, it is of at most 425 μm; most preferably, it is of at most 355 μm.

$D_{max,2}$ may be notably of at most 200 μm, at most 150 μm or at most 100 μm. Preferably, $D_{max,2}$ is of at most 212 μm; more preferably, it is of at most 180 μm; still more preferably, it is of at most 150 μm.

$D_{min,3}$ may be notably of at least 75 μm, at least 100 μm, at least 125 μm, at least 150 μm, at least 175 μm, at least 200 μm, etc. $D_{min,3}$ is preferably of at least 63 μm; more preferably, it is of at least 90 μm; still more preferably, it is of at least 112 μm.

$D_{max,4}$, $D_{max,5}$ and $D_{min,6}$ may comply with any of the limitations as above expressed for $D_{max,1}$, $D_{max,2}$ and $D_{min,3}$ respectively.

The terms "making the commerce" should be understood in their broadest meaning. This includes notably the act of offering for sale, and/or the act of selling the light sodium carbonate of concern.

The public disclosure may be oral or in written form. In particular, it can be in the form of a product data sheet. It can be contained in a written offer for sale or sales agreement.

Insofar as the present method for making commerce is concerned, the terms "characteristic", "exemplary", "normal", "regular", "representative", "sample", "typic", "ordinary", "mean", "average", "median", "central", "mesial", "modal" and the like should be considered as having the same meaning as the term "typical". Thus, for example, a method for making the commerce of a light sodium carbonate which comprises making publicly available the explicit information that the particle size distribution of the light sodium carbonate has the following characteristic or exemplary or normal or regular or representative or sample or typic or ordinary or mean or average or median or central or mesial or modal value:

$$D_{99.5} = D_{max,4} \text{ μm} \qquad (S4)$$

wherein $D_{max,4}$ can be any integer $\leq 630$ μm, is also a method (M) in accordance with the present invention.

The information that the light sodium carbonate complies with the sale specifications or typical values (S1), (S2), (S3), (S4), (S5) and (S6), when present, may be implicitly or inherently contained in the information (I1), (I2), (I3), (I4), (I5) and (I6). One example of the available information content of a document extending beyond its explicit content, is the case where the carrying out of a process for making a light sodium carbonate, explicitly described in a document, inevitably results in a light sodium carbonate product having certain sale specifications or typical values not so described.

In a certain embodiment, the information that the light sodium carbonate complies with the sale specifications or typical values (S1), (S2), (S3), (S4), (S5) and (S6), when present, can be derived directly and unambiguously from the information (I1), (I2), (I3), (I4), (I5) and (I6) respectively. Thus, typically, in accordance with said embodiment, a person skilled in the art, having knowledge of any of the information (I1), ($I_2$), (I3), (I4), (I5) and (I6), can derive directly and unambiguously therefrom that the information that the light sodium carbonate complies with the sale specifications or typical values (S1), (S2), (S3), (S4), (S5) and (S6) respectively; for the sake of easiness, the information (I1), (I2), (I3), (I4), (I5) and (I6), when present, are advantageously contained in a single document or oral disclosure.

As an example of information from which it can be directly and unambiguously derived that the light sodium carbonate complies with the sales specification (S1), it can be cited the sales specification (S1') wherein the weight of the light sodium carbonate having a diameter of at least $D_{max,1}$ μm is of at most 0.5%, based on the total weight of the light sodium carbonate. In particular, when a sieving method is used, it can be mentioned as a sales specification in the product data sheet: "wt. % refused on 710 μm-sieve $\leq 0.5$%", or "wt. % refused on 630 μm-sieve $\leq 0.5$%", or the like.

As an example of information from which it can be directly and unambiguously derived that the light sodium carbonate complies with the sales specification (S2), it can be cited the sales specification (S2') wherein the weight of the light sodium carbonate having a diameter of at least $D_{max,2}$ μm is of at most 10%, based on the total weight of the light sodium carbonate. In particular, when a sieving method is used, it can be mentioned as a sales specification in the product data sheet: "wt. % refused on 250 μm-sieve $\leq 10$%", "wt. % refused on 224 μm-sieve $\leq 10$%", or the like.

As an example of information from which it can be directly and unambiguously derived that the light sodium carbonate complies with the sales specification (S3), it can be cited the sales specification (S3') wherein the weight of the light sodium carbonate having a diameter of at most $D_{min,3}$ μm is of at most 10%, based on the total weight of the light sodium carbonate. In particular, when a sieving method is used, it can be mentioned as a sales specification in the product data sheet: "wt. % passed on 45 μm-sieve $\geq 10$%", "wt. % passed on 63 μm-sieve $\geq 10$%", or the like.

As an example of information from which it can be directly and unambiguously derived that the light sodium carbonate has the typical analytical value in accordance with relationship (S4)

$$D_{99.5} = D_{max,4} \text{ μm} \qquad (S4)$$

wherein $D_{max,4}$ can be any integer $\leq 630$ µm, it can be cited the information (S4') wherein the weight of the light sodium carbonate having a diameter of at least $D_{max,4}$ µm is typically of at most 0.5%, based on the total weight of the light sodium carbonate. In particular, when a sieving method is used, it can be mentioned as a typical value in the product data sheet: "wt. % refused on 630 µm-sieve ≤0.5%", or "wt. % refused on 500 µm-sieve ≤0.5%", or the like.

Finally, as will be detailed below, there are certain specialty sodium carbonates, distinct from light sodium carbonates and from dense sodium carbonates, which have generally the appropriate particle size requirements:

$D_{90} \geq 45$ µm and $D_{90} \leq 250$ µm and $D_{99.5} \leq 710$ µm.

These ones have a free flowing density in-between that of light soda ash and that of dense soda ash; the free flowing density of said specialty sodium carbonates, as measured in accordance with ISO 903 standard, is generally from 0.65 kg/dm³ to 0.80 kg/dm³, often from 0.65 kg/dm³ to 0.75 kg/dm³, and typically of about 0.70 kg/dm³. They can be obtained notably by re-dissolving in water a light sodium carbonate obtained by the SOLVAY® process, re-precipitating sodium bicarbonate ($NaHCO_3$) by the addition of $CO_2$, isolating the precipitate (typically by centrifugation), calcinating the isolated precipitate to form a sodium carbonate, and screening the formed sodium carbonate through a sieve having meshes of the appropriate size, to form said specialty sodium carbonates.

SODASOLVAY® IPH sodium carbonate, as commercialized by SOLVAY SA, is an example of such specialty sodium carbonate having generally the appropriate particle size distribution requirements.

The Applicant has further found that the presence of calcium in the sodium carbonate could affect certain properties of the PAEKs, e.g. their final metal content; in particular, calcium as originating from the sodium carbonate was found to be immobilized in the PAEK as $CaF_2$. Accordingly, the sodium carbonate in accordance with the present invention has a calcium weight content, expressed in CaO, of usually at most 450 ppm, preferably at most 150 ppm, more preferably at most 100 ppm, and still more preferably at most 75 ppm. With this regard, using SODASOLVAY® L is especially attractive as it contains typically from about 35 to about 60 ppm of calcium, expressed as CaO; on the other hand, SODASOLVAY® IPH sodium carbonate contains typically about 170 ppm of calcium, expressed as CaO.

Referring back to the method for making the commerce of a light sodium carbonate as above described, certain preferred embodiments thereof comprise thus making publicly available, in any form and by any means, and/or providing to at least one customer, whatever bound to any confidentiality obligations or not, at least one of the following information:

the explicit information that the light sodium carbonate complies with the following sales specification concerning its calcium weight content, expressed in CaO:

$$\text{CaO content} \leq Q_{max,7} \text{ ppm} \tag{S7}$$

wherein $Q_{max,7}$ can be any integer $\leq 150$ ppm;

the information (I7) from which it can be derived that the light sodium carbonate complies with the sales specifications (S7);

the explicit information that the calcium content of the light sodium carbonate, expressed in CaO, has as typical analytical value:

$$\text{CaO content} \leq Q_{max,8} \text{ ppm} \tag{S8}$$

wherein $Q_{max,8}$ can be any integer $\leq 100$ ppm;

the information (18) from which it can be derived that the light sodium carbonate has the typical analytical value (S8), and any combination thereof.

Preferably, $Q_{max,7}$ is of at most 100 ppm; more preferably, it is of at most 75 ppm.

Preferably, $Q_{max,8}$ is of at most 75 ppm; more preferably, it is of at most 60 ppm.

The information that the light sodium carbonate complies with the sale specification (S7) and the typical value (S8), when present, may be implicitly or inherently contained in the information (I7) and (I8) respectively. In a certain embodiment, the information that the light sodium carbonate complies with the sale specification (S7) and the typical value (S8), when present, can be derived directly and unambiguously from the information (I7) and (I8) respectively.

To a less extent, the content of certain other metals, like iron and magnesium, should also be maintained at a low level. Thus, accordingly, the sodium carbonate in accordance with the present invention has a magnesium weight content, expressed in MgO, of preferably of below 450 ppm, more preferably below 150 ppm, and still more preferably below 75 ppm. With this regard, using SODASOLVAY® L is also especially attractive as it contains typically from about 20 ppm to about 65 ppm of calcium, expressed as MgO. As concerns iron, its weight content in the sodium carbonate in accordance with the present invention, expressed as $Fe_2O_3$, is preferably of at most 100 ppm, more preferably below 30 ppm, and still more preferably below 15 ppm. Again, using SODASOLVAY® L is especially attractive as it contains typically from about 3 to about 10 ppm of iron, expressed as $Fe_2O_3$.

An important and surprising benefit resulting from the use of sodium carbonate powder meeting the above described requirements is that it allows one to limit the amount of potassium carbonate, and more generally of any other higher alkali metal carbonate, to be used in the preparation of the PAEK. As higher alkali metal carbonates other than potassium carbonate, it can be particularly cited rubidium carbonate and caesium carbonate.

Thus, the molar ratio of K/Na can be of at most 0.050 mol K/mol Na, preferably at most 0.020 mol K/mol Na, and more preferably at most 0.010 mol K/mol Na. In an especially surprising particular embodiment, the molar ratio of K/Na is equal to 0 (i.e. the nucleophilic substitution takes place in the absence of potassium carbonate); said particular embodiment is usually preferred when the PAEK is a PEK polymer, notably when it is a PEK homopolymer as defined hereinafter. In another embodiment, to which the preference is often given, notably when the PAEK is a PEEK polymer such as a PEEK homopolymer, the molar ratio of K/Na, although being maintained at a low level (e.g. in accordance with the above specified upper limits), is above 0, preferably of at least 0.001 mol K/mol Na, more preferably of at least 0.002 mol K/mol Na and still more preferably of at least 0.003 mol K/mol Na.

More generally, the molar ratio of A/Na (wherein A designates either K, Cs or Rb or any combination thereof) can be of at most 0.050 mol A/mol Na, preferably at most 0.020 mol A/mol Na, and more preferably at most 0.010 mol A/mol Na. In an especially surprising particular embodiment, the molar ratio of A/Na is equal to 0 (i.e. the nucleophilic substitution takes place in the absence of potassium carbonate); said particular embodiment is usually preferred when the PAEK is a PEK polymer, notably when it is a PEK homopolymer as defined hereinafter. In another embodiment, to which the preference is often given, notably when the PAEK is a PEEK polymer such as a PEEK homopolymer, the molar ratio of A/Na, although being maintained at a low level (e.g. in accordance with the above specified upper limits), is above 0, preferably of at least 0.001 mol A/mol Na, more preferably of at least 0.002 mol A/mol Na and still more preferably of at least 0.003 mol A/mol Na.

The Applicant has also surprisingly found that, contrarily to the particle size distribution of the sodium carbonate, the particle size distribution of the potassium carbonate, when present, was not critical at all, although a slight additional improvement in terms of polymerization kinetics might be observed when using a very finely ground potassium carbonate. Thus, suitable potassium carbonates, when used in the method for preparing PAEKs in accordance with the presence invention, may have a particle size distribution, including any of the following characteristics, or any combination thereof:

$D_{99.5} \leq 1000$ μm, or $D_{99.5} \leq 800$ μm, or $D_{99.5} \leq 600$ μm, or $D_{99.5} \leq 400$ μm, or $D_{99.5} \leq 200$ μm, or $D_{99.5} \leq 100$ μm, or $D_{99.5} \leq 45$ μm, or $D_{99.5} \leq 30$ μm, or $D_{99.5} \leq 15$ μm, etc.

$D_{99.5} \geq 5$ μm, or $D_{99.5} \geq 10$ μm, or $D_{99.5} \geq 15$ μm, or $D_{99.5} \geq 30$ μm, or $D_{99.5} \geq 45$ μm, or $D_{99.5} \geq 100$ μm, etc.

$D_{90} \leq 1000$ μm, or $D_{90} \leq 800$ μm, or $D_{90} \leq 600$ μm, or $D_{90} \leq 400$ μm, or $D_{90} \leq 200$ μm, or $D_{90} \leq 100$ μm, or $D_{90} \leq 45$ μm, or $D_{90} \leq 30$ μm, or $D_{90} \leq 15$ μm, or $D_{90} \leq 10$ μm, etc.

$D_{90} \geq D_{90} \geq 5$ μm, or $D_{99} \geq 10$ μm, or $D_{90} \geq 15$ μm, or $D_{90} \geq 30$ μm, or $D_{90} \geq 45$ μm, or $D_{99} \geq 100$ μm, etc.

Any of the above expressed limitations concerning the upper limit for $D_{99.5}$, the lower limit for $D_{99.5}$, the upper limit for $D_{90}$, and the lower limit for $D_{90}$ of the potassium carbonate, can be combined with each other to provide a suitable potassium carbonate. Non limitative examples of such combinations include:

$D_{90} \geq 2.5$ μm and $D_{99.5} \leq 45$ μm, and
$D_{90} \geq 10$ μm and $D_{99.5} \leq 200$ μm.
$D_{90} \geq 2.5$ μm and $D_{90} \leq 25$ μm, and
$D_{90} \geq 10$ μm and $D_{99} \leq 100$ μm.

The term "poly(aryletherketone)" (PAEK) as used herein includes any polymer of which more than 50 wt. % of the recurring units are recurring units (R1) of one or more formulae containing at least one arylene group, at least one ether group (—O—) and at least one ketone group [—C(=O)—].

Preferably, recurring units (R1) are chosen from:

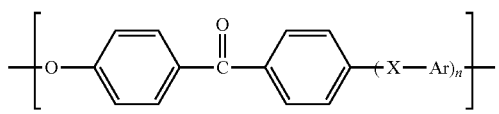

(I)

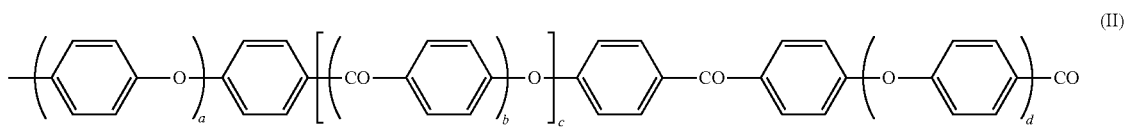

(II)

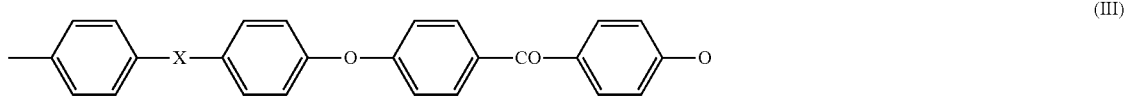

(III)

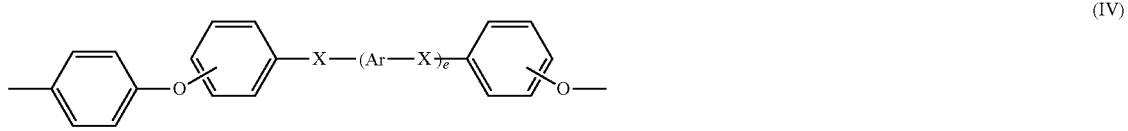

(IV)

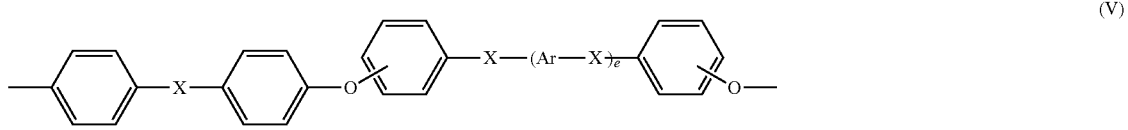

(V)

wherein:
Ar is independently a divalent aromatic radical selected from phenylene, biphenylene or naphthylene,
X is independently O, C(=O) or a direct bond,
n is an integer of from 0 to 3,
b, c, d and e are 0 or 1,
a is an integer of 1 to 4, and
preferably, d is 0 when b is 1.
More preferably, recurring units (R1) are chosen from:
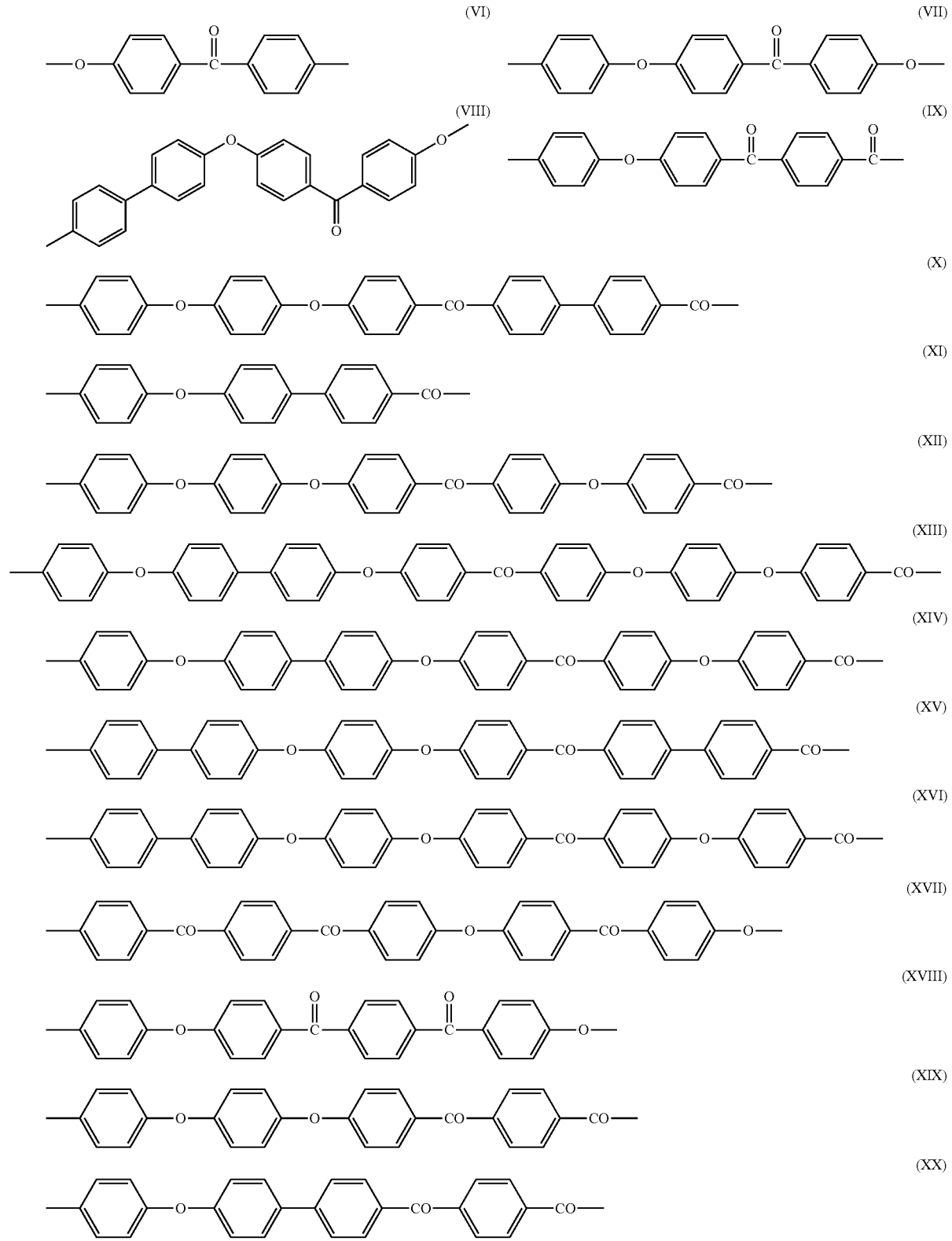

-continued

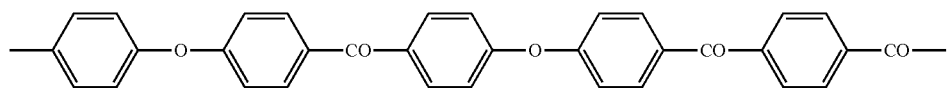
(XXI)

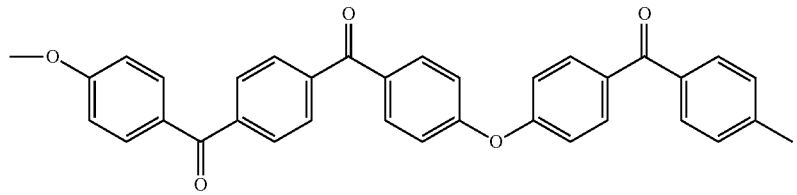
(XXII)

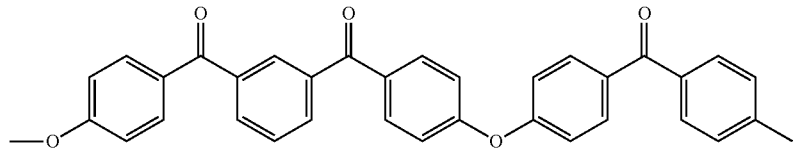
(XXIII)

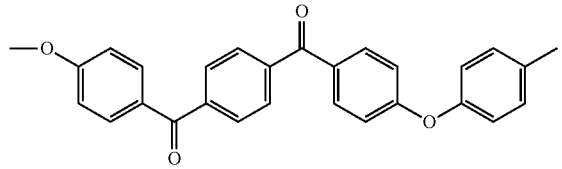
(XXIV)

(XXV)

Still more preferably, recurring (R1) are chosen from:

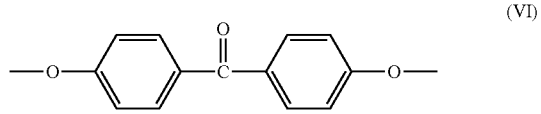
(VI)

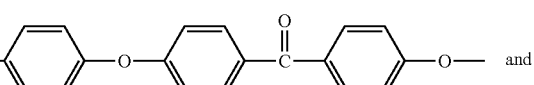
(VII)

and

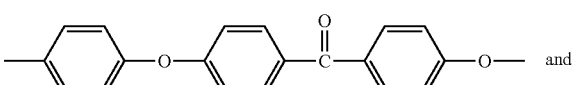
(VIII)

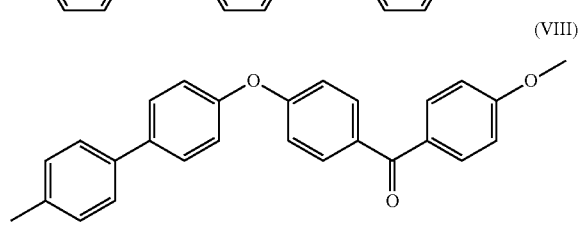

Most preferably, recurring units (R1) are:

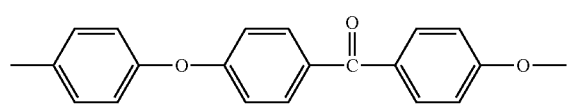
(VII)

A PEEK polymer is intended to denote any polymer of which more than 50 wt. % of the recurring units are recurring units (R1) of formula (VII). A PEK polymer is intended to denote any polymer of which more than 50 wt. % of the recurring units are recurring units (R1) of formula (VI).

A PEEK homopolymer is intended to denote any polymer of which essentially all (if not, all) the recurring units are recurring units (R1) of formula (VII). A PEK homopolymer is intended to denote any polymer of essentially all (if not, all) the recurring units are recurring units (R1) of formula (VI).

The poly(aryl ether ketone) may be notably a homopolymer, a random, alternate or block copolymer. When the poly (aryletherketone) is a copolymer, it may notably contain (i) recurring units (R1) of at least two different formulae chosen from formulae (VI) to (XXV), or (ii) recurring units (R1) of one or more formulae (VI) to (XXV) and recurring units (R1*) different from recurring units (R1).

Preferably more than 70 wt. %, more preferably more than 85 wt. % of the recurring units of the poly(aryletherketone) are recurring units (R1). Still more preferably, essentially all the recurring units of the poly(aryletherketone) are recurring units (R1). Most preferably, all the recurring units of the poly(aryletherketone) are recurring units (R1).

As noted above, PAEKs are generally prepared by aromatic nucleophilic substitution. In a preferred embodiment, in the method according to the present invention, an aromatic diol, which can be selected from the group consisting of hydroquinones, bisphenols and mixtures thereof, is deprotonated with sodium carbonate of a particle size as described herein, and the resultant phenoxide may then react with, e.g., a dihalobenzophenone via nucleophilic substitution. Semi-crystalline PAEKs prepared by such a nucleophilic substitution method, particularly in the absence of a cosolvent forming an azeotrope with water, using the invention sodium carbonate optionally in admixture with another base such as potassium carbonate, make up a part of this invention, as does their method of preparation.

PAEKs prepared according the invention using the invented sodium carbonate have advantageously the following color characteristics:

Powder color L*>85, preferably L*>86, more preferably L*>87;

Powder color a* is in the range of −1 to 2, preferably −1<a*<2, more preferably −0.5<a*<1.5, most preferably, a* is the range of from 0.0 to 1.0;

Powder color b* is from 2 to 18, more preferably from 4 to 16.

where powder color is measured on ground polymer using the CIE Lab standards, as follows: The color is generally characterized by L*, a*, b* values, which are tristimulus coordinates defined by the CIE (Commission Internationale de l'Eclairage) in 1976 (K. Nassau, in "Kirk-Othmer Encyclopedia of Chemical Technology", 2004, Chapter 7, P 303-341). These three basic coordinates represent the lightness of the color (L*, L*=0 yields black and L*=100 indicates white), its position between red/magenta and green (a*, negative values indicate green while positive values indicate magenta) and its position between yellow and blue (b*, negative values indicate blue and positive values indicate yellow).

The color of the powder of a given particle size ($D_{50}$ of ground polymer 200-500 μm) is measured according to ASTM E308-06 using Cool White Fluorescent as illuminant at 10° angle (1964 CIE). All measurements were made on Gretag Macbeth Color Eye Ci5 Spectrophotometer, with tribeam diffuse/8" 6" sphere optical geometry, a bandpass of 10 nm, a spectral range of 360 nm to 750 nm. Powders were placed in a colorimeter quartz cell. Ten readings were taken at different angles and the average value is given. No bandpass correction was applied.

As explained above, the present invention enables an excellent synthesis of PAEKs in the absence of a cosolvent forming an azeotrope with water, thereby producing PAEKs having less than or equal to 10 ppm residual agent, such as p-xylene, preferably less than or equal to 5 ppm residual agent, the PAEKs most preferably being free of residual agent. Residual agent can be measured for example by gas chromatography of acetone extracts of the PAEKs as described in the examples. Moreover, in a preferred embodiment the PAEKs produced with the invention sodium carbonate preferably provide reduced viscosity (RV) values measured at 25° C. with 1 wt./vol. % in conc. sulfuric acid of greater than or equal to 0.70 dl/g RV, including 1.1, 1.2, 1.3, 1.4, 1.5, 1.6, 1.7, 1.8, 1.9. 2.0, 2.1, 2.2, 2.3, 2.4, 2.5, 2.6, 2.7, etc. dl/g, a preferred range of RV being 0.70-2.0 dl/g.

The PAEK prepared by the method in accordance with the present invention can be shaped into various articles, absent any additive. Alternatively, before being shaped into an article, it can be mixed with a variety of additives, in particular all these ingredients which are commonly used for the preparation of a PAEK composition, such as reinforcing agents such as glass fiber and carbon fiber, lubricating and/or anti-wear agents such as polytetrafluoroethylene, heat stabilizers, anti-static agents, extenders, organic and/or inorganic pigments like $TiO_2$, carbon black, acid scavengers such as MgO, stabilizers (e.g. metal oxides and sulfides, such as zinc oxide and zinc sulfide), antioxidants, flame retardants, smoke-suppressing agents, and particulate fillers and nucleating agents such as talc, mica, titanium dioxide, kaolin and the like. Thus, it is another object of the present invention to provide a composition comprising the PAEK prepared by the above described method, and at least one other ingredient; and it is still another object of the present invention to provide a shaped article comprising the PAEK prepared by the above described method, or the composition as above described. With this regard, as non limitative examples of shaped article in accordance with the present invention, it can be cited:

shaped articles which can be used in the semiconductor industry, such as wafer handling, test sockets, IC trays and semiconductor assemblies;

shaped articles which can be used in the automotive field such as fuel tubes and static paintings;

friction and wear components such as bearings;

medical components, such as catheters, implants and orthopedic tools.

The present invention is described in greater detail below by referring to the examples; however, the present invention is not limited to these examples.

EXAMPLES

Particle Size Distribution (PSD) of $Na_2CO_3$ Determined by Mechanical Sieving

The analysis is based on the mechanical separation of the various fractions on a series of superimposed sieves. The content of each sieve is weighed, and the fraction of sample collected is reported to the total quantity of sample.

Apparatus:
   Mechanical sieving apparatus able to transmit combined movements in the horizontal plane and shocks along the vertical axis to a pile of superimposed sieves (apparatus used: RO-TAP RX-29 Model or equivalent, with 278 horizontal revolutions and 150 taps per minute)
   Series of circular sieves, wire stainless steel with square meshes, metal mounting with a diameter 200 mm, in conformity with NF ISO 3310-1 standard and periodically checked using a reference powder.

Sieves superimposed by descending order of opening mesh (size in μm): 1000 μm, 500 μm, 250 μm, 180 μm, 125 μm, 90 μm, 63 μm and 45 μm.

Analytical balance, accuracy 0.01 g.

Method:
   Test Specimen: 70 g of powder weighed to 0.01 g.
   Transfer the test specimen on the pile of sieves and position it in the apparatus
   Sieve for 15 minutes.
   Weigh the content of each sieve to 0.01 g.

Calculation:
   Calculate the weight percentage of the test specimen retained on each sieve.
   Express the weight percentage passing through each sieve, and cumulated.
   Determine by graphical interpolation the mesh opening equivalent to the 90% and 99.5% cumulated weight percentage ($D_{90}$, $D_{99.5}$)

RV Measurement Conditions:
   Reduced Viscosity (RV) was measured according ASTM D2857-95 (2007) at 25° C. in concentrated sulfuric acid (1 wt. %/vol.). The viscometer tube was number 50 Cannon Fenske. The solution used was prepared by dissolving 1.0000±0.0004 g of resin in 100 ml±0.3 ml concentrated sulfuric acid (95-98%, density=1.84). In order to facilitate the dissolution, ground powder (approx mean particle size 200-600 μm) was used. The sample was dissolved at room temperature (no heating).

The solution was filtered on glass frit (medium porosity) before use. The RV was calculated as $$RV = \frac{t_{soln} - t_{solvent}}{t_{solvent} * C}$$

wherein $t_{soln}$ and $t_{solvent}$ are the efflux times measured for the solution and the blank solvent, respectively.

Since sulfonation of the polymer can occur in concentrated sulfuric acid, the efflux time of the solution has to be measured within the 3 hours after the preparation of the solution.

The average of at least 3 measurements was used for efflux times. Under these conditions, the efflux times should be longer than 200 s and, no correction for kinetic energy was applied.

Determination of Residual p-xylene in a PAEK by GC

The ground polymer (0.6 g) was extracted with acetone (5 ml) by shaking in a 20 ml vial for 2 hours. The acetone extract was centrifuged and analyzed by GC under the following conditions.

GC Instrument and Conditions

HP 5890 or Agilent 6890 Gas Chromatograph with autosampler and Chemstation software.

Column: HP-5, 15 m, 0.25 mm ID and film thickness of 0.25 μm df

Oven Temperature Program: Initial temperature 120° C. with 1 minute hold, program rate of 30° C./minute to 325° C., with 1 minute hold at 325° C.

Injection amount: 1.0 μl

Injector temperature: 300° C.

Detector temperature: 300° C.

Split ratio: 80:1 p-xylene has typically a retention time of 1.4 minutes and its concentration was determined with an external standard of commercially available p-xylene. Its concentration is expressed in weight p-xylene/total weight polymer plus impurities.

Other common cosolvents (chlorobenzene, toluene, etc) can be analyzed using the same technique. Use of commercially available standards allows the determination of the retention time and response factor.

Determination of Ca, Mg and Fe Content of $Na_2CO_3$.

4.53 g of anhydrous $Na_2CO_3$ were introduced in a plastic beaker. 16 ml of 6N HCl (obtained by dilution of ultra pure 12 N HCl Merck 317 with Milli-Q water, resistivity ≥18 MΩ·cm) and 33 ml of Milli-Q water. The concentration in Ca was determined by ICP-AES at 317.933 nm using external standards. The concentration in Mg was determined by ICP-AES at 280.270 nm using external standards. The concentration in Fe was determined by ICP-AES at 238.204 nm using external standards. The standard solutions were prepared by dilution of commercial standards (Ca: 1.000 g/l, CHEMLAB: CL01.0311.0500 HIQU, Mg: 1.000 g/l, CHEMLAB: CL01.1301.0500 HIQU, Fe: 1.000 g/l, CHEMLAB: CL01.0901.0500 HIQU) in 100 g/l aq. NaCl solution (prepared with Milli-Q water and ultra pure NaCl Merck 6406).

General Procedure Examples 1 Through 9 with 0.05 mol K/mol Na

In a 500 ml 4-neck reaction flask fitted with a stirrer, a $N_2$ inlet dip tube, a Claisen adapter with a thermocouple plunging in the reaction medium, and a Dean-Stark trap with a condenser and a dry ice trap were introduced 175.00 g of diphenyl sulfone [meeting all the impurity limitations of embodiment (E)], 28.0000 g of p-hydroquinone, 57.1200 g of 4,4'-difluorobenzophenone (containing 2,4'-difluorobenzophenone and 4-monofluorobenzophenone in a cumulated amount of at most 1250 ppm), 26.7700 g (0.253 mol) of dry $Na_2CO_3$ having the features as detailed in table 1 hereinafter, and 1.8000 g (0.013 mol) of dry $K_2CO_3$ having the technical features as detailed in table 2 hereinafter. The flask content was evacuated under vacuum and then filled with nitrogen 4 times using a Firestone valve and then placed under a nitrogen purge (30 ml/min). The reaction mixture was heated slowly to 200° C. (1 hour heating period) and held at 200° C. for 30 minutes then heated up to 250° C., held at 250° C. for 30 minutes, heated up to 310° C. and held at this temperature until an RV >0.70 was attained as measured by the reaction mixture viscosity or for 3 hours, whichever comes first. Termination was carried out by adding 1.4200g 4,4'-difluorobenzophenone (containing 2,4'-difluorobenzophenone and 4-monofluorobenzophenone in a cumulated amount of at most 1250 ppm) and 2.2100 g LiCl to the reaction mixture and keeping the mixture at 310° C. for an additional 30 minutes. The reactor content was then poured from the reactor into a stainless steel pan and cooled. The solid was broken up and ground in a Brinkman grinder through a 2 min screen. Diphenyl sulfone and salts were extracted from the mixture with acetone and water. The polymer was then dried at 120° C. under vacuum for 12 hours.

Reduced viscosity (RV) was measured at 25° C., with 1 wt./vol. % in conc. sulfuric acid. The target for a high molecular weight was set at 0.70 dl/g RV. The reaction was deemed successful if an RV higher than 0.70 dl/g could be reached.

Examples 1 through 5 are provided for comparison, while examples 6 to 9 are in accordance with the invention.

Example 10

With 0.02 mol K/mol Na 127.82 g diphenylsulfone [meeting all the impurity limitations of embodiment (E)], 56.9570 g 4,4'-difluorobenzophenone (containing 2,4'-difluorobenzophenone and 4-mono fluorobenzophenone in a cumulated amount of at most 1250 ppm), 28.5983 g p-hydroquinone, 27.5570 g (0.260 mol) of dry $Na_2CO_3$ having the features as detailed in table 1 hereinafter, and 0.7180 g (0.052 mol) of dry $K_2CO_3$ having the features as detailed in table 2 hereinafter were mixed under nitrogen at 150° C. The reaction mixture was heated slowly to 200° C. (1 hour heating period) and held at 200° C. for 30 minutes then heated up to 250° C., held at 250° C. for 30 minutes, heated up to 310° C. and held at this temperature for 30 minutes. End capping was carried out by adding 1.4150 g 4,4'-difluorobenzophenone (containing 2,4'-difluorobenzophenone and 4-monofluorobenzophenone in a cumulated amount of at most 1250 ppm) and, 65 minutes later, 1.8720 g LiCl to the reaction mixture and keeping the mixture at 310° C. for an additional 30 minutes. The reactor content was then poured from the reactor into a stainless steel pan and cooled. The solid was broken up and ground in a Brinkman grinder through a 2 mm screen. Diphenyl sulfone and salts were extracted from the mixture with acetone and water. The polymer was then dried at 120° C. under vacuum for 12 hours.

Reduced viscosity (RV) was measured at 25° C., with 1 wt./vol. % in conc. sulfuric acid. The target for a high molecular weight was set at 0.70 dl/g RV. The reaction was deemed successful if an RV higher than 0.70 dl/g could be reached.

Example 10 is in accordance with the invention.

Examples 11 Through 16

With 0.005 mol K/mol $Na_2CO_3$

In a 500 ml 4-neck reaction flask fitted with a stirrer, a $N_2$ inlet tube, a Claisen adapter with a thermocouple plunging in the reaction medium, and a Dean-Stark trap with a condenser and a dry ice trap were introduced 127.82 g of diphenyl sulfone [meeting all the impurity limitations of embodiment (E)], 28.5983 g of p-hydroquinone (dry basis) and 57.2337 g of 4,4'-difluorobenzophenone (containing 2,4'-difluorobenzophenone and 4-monofluorobenzophenone in a cumulated amount of at most 1250 ppm). The flask content was evacuated under vacuum and then filled with high purity nitrogen (containing less than 10 ppm $O_2$). The operation was repeated twice. The reaction mixture was then placed under a constant nitrogen purge (60 ml/min). The reaction mixture was heated slowly to 150° C. At 150° C., a mixture of 28.4259 g (0.268 mol) of dry $Na_2CO_3$ having the features as detailed in table 1 hereinafter, and 0.1800 g (0.0013 mol) of dry $K_2CO_3$ having the features as detailed in table 2 hereinafter was added via a powder dispenser to the reaction mixture over 30 minutes. At the end of the addition, the reaction mixture was heated to 320° C. at 1° C./minute. After 50 minutes at 320° C., 6.8203 g of 4,4'-difluorobenzophenone (containing 2,4'-difluorobenzophenone and 4-monofluorobenzophenone in a cumulated amount of at most 1250 ppm) were added to the reaction mixture while keeping a nitrogen purge on the reactor. After 5 minutes, 0.4420 g of lithium chloride were added to the reaction mixture. 10 minutes later, another 2.2734 g of 4,4'-difluorobenzophenone were added to the reactor and the reaction mixture was kept at temperature for 15 minutes. The reactor content was then poured from the reactor into a SS pan and cooled. The solid was broken up and ground in an attrition mill through a 2 mm screen. Diphenyl sulfone and salts were extracted from the mixture with acetone and water at pH between 1 and 12. The last wash water had a pH between 6 and 7. The powder was then removed from the reactor and dried at 120° C. under vacuum for 12 hours yielding 66.95 g of a white powder.

Reduced viscosity (RV) was measured at 25° C., with 1 wt./vol. % in conc. sulfuric acid. The target for a high molecular weight was set at 0.70 dl/g RV. The reaction was deemed successful if an RV higher than 0.70 dl/g could be reached.

Examples 11 and 12 are provided for comparison, while examples 13 to 16 are in accordance with the invention.

Where a specific value is given for a particle size $D_{xx}$ it means that xx % of the contained particles in the sample have the identified size or less.

TABLE 1

Description of the particulate $Na_2CO_3$ used in the examples

| Examples | Description of the participate $Na_2CO_3$ that were used |
|---|---|
| 1 to 3 | Aldrich ACS reagent, 99.95-100.05%, $Na_2CO_3$, having a $D_{99.5}$ of 900 μm, a $D_{90}$ of 700 μm and a $D_{50}$ of 258 μm as measured by mechanical sieving |
| 4 | Fraction of the Aldrich ACS reagent, 99.95-100.05%, $Na_2CO_3$ as used in examples 1 to 3, that was retained on a 250 μm sieve; the $Na_2CO_3$ of example 4 has a $D_{99.5}$ of 900 μm, a $D_{90}$ of 820 μm and a $D_{50}$ of 395 μm as measured by mechanical sieving |
| 5 | The SODASOLVAY ® L sodium carbonate of examples 7, 8, 10 and 13 to 16, that was finely ground; the so-ground $Na_2CO_3$ has a $D_{99.5}$, a $D_{90}$ and a $D_{50}$ below 50 μm |
| 6 | Fraction of the Aldrich ACS reagent, 99.95-100.05%, $Na_2CO_3$ as used in examples 1 to 3, that was screened through a 250 μm sieve; the $Na_2CO_3$ of example 6 has a $D_{99.5}$ of 249 μm, a $D_{90}$ of 219 μm and a $D_{50}$ of 141 μm, as measured by mechanical sieving |
| 7, 8, 10 and 13 to 16 | Selected lot of SODASOLVAY ® L light soda ash commercially available from SOLVAY SA (Dombasle plant), having a $D_{99.5}$ of 335 μm, a $D_{90}$ of 135 μm and a $D_{50}$ of 43 μm, as measured by mechanical sieving; it contains 27 ppm Ca, 13 ppm Mg and 4 ppm Fe (all quantities expressed as metal) |
| 9 | SODASOLVAY ® IPH pharmaceutical grade $Na_2CO_3$ commercially available from SOLVAY SA (Dombasle plant), having a $D_{99.5}$ of 180 μm, a $D_{90}$ of 137 μm and a $D_{50}$ of 98 μm; it contains 119 ppm Ca, 13 ppm Mg and less than 1 ppm $Fe_2O_3$ (all quantities expressed as metal) |
| 11 | Fraction of the Aldrich ACS reagent, 99.95-100.05%, $Na_2CO_3$ as used in examples 1 to 3, that was screened through a 500 μm sieve; the $Na_2CO_3$ of example 11 has a $D_{99.5}$ of 579 μm, a $D_{90}$ of 462 μm and a $D_{50}$ of 298 μm, as measured by mechanical sieving |
| 12 | Fraction of the Aldrich ACS reagent, 99.95-100.05%, $Na_2CO_3$ as used in examples 1 to 3, that was screened through a 425 μm sieve; the $Na_2CO_3$ of example 12 has a $D_{99.5}$ of 498 μm, a $D_{90}$ of 445 μm and a $D_{50}$ of 239 μm, as measured by mechanical sieving |

TABLE 2

Description of the particulate $K_2CO_3$ used in the examples

| Examples | Description of the particulate $K_2CO_3$ that were used |
|---|---|
| 1 to 13 | "Extra fine glass grade" EF-90 $K_2CO_3$ commercially available from the Armand Products Company, having a $D_{99.5}$ of 75 μm, a $D_{90}$ of 28 μm and a $D_{50}$ of 14 μm, as measured by dynamic light scattering using a Microtrac ® S3500 analyzer (dry mode, 55 psi nitrogen) |
| 14 | Ground EF-80 $K_2CO_3$ grade available from the Armand Products Company, having a $D_{99.5}$ of 194 μm, a $D_{90}$ of 84 μm and a $D_{50}$ of 19 μm, as measured by dynamic light scattering using a Microtrac ® S3500 analyzer (dry mode, 55 psi nitrogen) |

TABLE 2-continued

Description of the particulate $K_2CO_3$ used in the examples

| Examples | Description of the particulate $K_2CO_3$ that were used |
|---|---|
| 15 | Aldrich $K_2CO_3$, ACS reagent, having a $D_{9.55}$ of 475 μm, a $D_{90}$ of 388 μm and a $D_{50}$ of 300 μm, as measured by dynamic light scattering using a Microtrac ® S3500 analyzer (dry mode, 55 psi nitrogen) |
| 16 | Aldrich $K_2CO_3$, reagent grade, powder-325 mesh, having a $D_{99.5}$ of 65 μm, a $D_{90}$ of 42 μm and a $D_{50}$ of 12 μm, as measured by dynamic light scattering using a Microtrac ® S3500 analyzer (dry mode, 55 psi nitrogen) |

Table 3 summarizes certain important technical features of the exemplified processes, and the RV of the formed PEEK

TABLE 3

Technical features of the examplified processes and PEEK RV

| Example | Co solvent forming an azeotrope with water | K/Na (mol/mol) | $Na_2CO_3$ $D_{99.5}$ (μm) | $Na_2CO_3$ $D_{90}$ (μm) | $Na_2CO_3$ $D_{50}$ (μm) | RV (dl/g) |
|---|---|---|---|---|---|---|
| C1 | p-xylene | 0.05 | 900 | 700 | 258 | 0.94 |
| C2 | p-xylene | 0.05 | 900 | 700 | 258 | 0.91 |
| C3 | — | 0.05 | 900 | 700 | 258 | 0.48 |
| C4 | — | 0.05 | 900 | 820 | 395 | 0.38 |
| C5 | — | 0.05 | <45 | <45 | <45 | 2.36 |
| 6 | — | 0.05 | 249 | 219 | 141 | 0.82 |
| 7 | — | 0.05 | 335 | 135 | 43 | 1.60 |
| 8 | — | 0.05 | 335 | 135 | 43 | 1.86 |
| 9 | — | 0.05 | 180 | 137 | 98 | 1.08 |
| 10 | — | 0.02 | 335 | 135 | 43 | 0.99 |
| C11 | — | 0.005 | 579 | 462 | 298 | 0.37 |
| C12 | — | 0.005 | 498 | 445 | 239 | 0.35 |
| 13 | — | 0.005 | 335 | 135 | 43 | 0.89 |
| 14 | — | 0.005 | 335 | 135 | 43 | 1.18 |
| 15 | — | 0.005 | 335 | 135 | 43 | 1.19 |
| 16 | — | 0.005 | 335 | 135 | 43 | 1.23 |

Table 4 shows the powder color, color characteristics, residual cosolvent content, and RV.

TABLE 4

Characterization of the PEEK prepared according to examples 1 to 16

| Example | Powder color | L* | a* | b* | [p-xylene] in final powder (ppm) | RV (dl/g) |
|---|---|---|---|---|---|---|
| C1 | Off white | | | | >10 | 0.94 |
| C2 | Light pink | 87.04 | 2.17 | 6.95 | >10 | 0.91 |
| C3 | Off white | | | | <10 | 0.48 |
| C4 | Off white | | | | <10 | 0.38 |
| C5 | Off white | 88.61 | 0.32 | 4.78 | <10 | 2.36 |
| 6 | Off white | | | | <10 | 0.82 |
| 7 | White | 91.93 | 0.44 | 5.1 | <10 | 1.60 |
| 8 | Off white | 89.15 | 0.40 | 5.13 | <10 | 1.86 |
| 9 | Off White | 85.49 | 0.64 | 7.54 | <10 | 1.08 |
| 10 | White | 90.40 | 0.15 | 4.92 | <10 | 0.99 |
| C11 | Off white | | | | <10 | 0.37 |
| C12 | Off white | | | | <10 | 0.35 |
| 13 | White | 85.26 | 0.43 | 6.87 | <10 | 0.89 |
| 14 | White | 88.54 | 0.22 | 6.75 | <10 | 1.18 |
| 15 | White | 88.51 | 0.23 | 6.76 | <10 | 1.19 |
| 16 | White | 89.91 | 0.24 | 5.97 | <10 | 1.23 |

Examples C1 and C2 show that, using Aldrich ACS reagent, 99.95-100.05%, $Na_2CO_3$ (not meeting the particle size requirements) and a cosolvent forming an azeotrope with water, high molecular weight PEEK can be obtained but residual p-xylene is detected and the 20 powder can be pink (a*>2).

C3 and C4 show that, with Aldrich ACS reagent, 99.95-100.05%, $Na_2CO_3$ or with a high-size fraction thereof (not meeting the particle size requirements), and in the absence of a cosolvent forming an azeotrope with water, only low molecular weight is obtained.

C11 and C12 show that using Aldrich ACS reagent, 99.95-100.05%, or a screened fraction thereof using a 500 μm or 425 μm sieve (not meeting the particle size requirements), and in the absence of a cosolvent forming an azeotrope with water, only low molecular weight is obtained.

C5 shows that, with finely ground light soda ash (not meeting the particle size requirements), and in the absence of a cosolvent forming an azeotrope with water, the reaction cannot be controlled and a very high molecular weight is attained in a very short time (about 5 minutes at 310° C.).

Example 6 (using Aldrich ACS reagent $Na_2CO_3$ screened through 250 μm Sieve, meeting the particle size requirements) and examples 7 and 8 (using a lot of a commercial unground light soda ash which meets also the particle size requirements) show that a good control of the reaction kinetics is possible and good quality (color, p-xylene) polymer is obtained.

Examples 13 through 16 show that, using light $Na_2CO_3$ a lot of a commercial unground light soda ash meeting the PSD requirements, high molecular weight, low color PEEK can be obtained with low levels of $K_2CO_3$. Different grades of $K_2CO_3$ were used and shown to give similar results.

The above written description of the invention provides a manner and process of making and using it such that any person skilled in this art is enabled to make and use the same, this enablement being provided in particular for the subject matter of the appended claims, which make up a part of the original description and including.

As used herein, the phrases "selected from the group consisting of," "chosen from," and the like include mixtures of the specified materials. Terms such as "contain(s)" and the like as used herein are open terms meaning 'including at least' unless otherwise specifically noted. Phrases such as "mention may be made," etc. preface examples of materials that can be used and do not limit the invention to the specific materials, etc., listed.

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein. In this regard, certain embodiments within the invention may not show every benefit of the invention, considered broadly.

The invention claimed is:

1. A method for the preparation of a poly(ether ether ketone) (PEEK), comprising:
preparing the PEEK by aromatic nucleophilic substitution in the presence of particulate sodium carbonate, wherein said particulate sodium carbonate has a particle size distribution as follows : $D_{90} \geq 45$ μm and $D_{90} \leq 250$ μm and $D_{99.5} \leq 710$ μm, wherein said particle size distribution is measured by mechanical sieving in accordance with ASTM E 359-00 (reapproved 2005), wherein said measurement is based on the mechanical separation of various fractions on a series of superimposed sieves which are superimposed by descending order of opening mesh of 1000 μm, 500 μm, 250 μm, 180 μm, 125 μ, 90 μm, 63 μm, and 45 μm.

2. The method according to claim 1, wherein said particulate sodium carbonate has a particle size distribution as follows: $D_{90} \geq 63$ μm and $D_{90} \leq 250$ μm.

3. The method according to claim 1, wherein said particulate sodium carbonate has a particle size distribution as follows: $D_{90} \leq 212$ μm and $D_{90} \geq 45$.

4. The method according to claim 1, wherein said particulate sodium carbonate has a particle size distribution as follows: $D_{99.5} \leq 500$ μm.

5. The method according to claim 1, wherein said particulate sodium carbonate has a particle size distribution as follows: $D_{90} \geq 45$ μm and $D_{90} \leq 180$ μm and $D_{99.5} \leq 425$ μm.

6. The method according to claim 1, wherein said particulate sodium carbonate has a calcium weight content, expressed in CaO, of at most 75 ppm.

7. The method according to claim 1, wherein the poly(ether ether ketone) produced has an $L^* > 87$.

8. The method according to claim 1, wherein the poly(ether ether ketone) produced has an $a^* < 2$.

9. The method according to claim 1, wherein the poly(ether ether ketone) is produced in a solvent and in the absence of p-xylene.

10. The method according to claim 9, wherein the poly(ether ether ketone) is produced in the absence of any cosolvent which forms an azeotrope with water.

11. The method according to claim 1, wherein the poly(ether ether ketone) is prepared in the presence of the particulate sodium carbonate and $K_2CO_3$, wherein $K_2CO_3$ is present in a ratio of no more than 0.01 mol K/mol Na.

12. The method according to claim 1, wherein said particulate sodium carbonate has a particle size distribution as follows: $D_{90} \geq 75$ μm and $D_{90} \leq 250$ μm and $D_{99.5} \leq 710$ μm.

13. The method according to claim 1, wherein the poly(ether ether ketone) is prepared in the presence of the particulate sodium carbonate and $K_2CO_3$, wherein $K_2CO_3$ is present in a ratio of no more than 0.05 mol K/mol Na.

* * * * *

UNITED STATES PATENT AND TRADEMARK OFFICE
CERTIFICATE OF CORRECTION

PATENT NO.         : 9,175,136 B2
APPLICATION NO.    : 13/125537
DATED              : November 3, 2015
INVENTOR(S)        : Chantal Louis Page 1 of 1

It is certified that error appears in the above-identified patent and that said Letters Patent is hereby corrected as shown below:

In the claims,
Claim 1, column 37, line 24, the phrase "125µ" should read -- 125µm --.

Signed and Sealed this
Twenty-second Day of March, 2016

Michelle K. Lee
*Director of the United States Patent and Trademark Office*